US012572894B2

(12) United States Patent
Nino et al.

(10) Patent No.: US 12,572,894 B2
(45) Date of Patent: Mar. 10, 2026

(54) METHOD TO INCREASE EFFICIENCY, COVERAGE, AND QUALITY OF DIRECT PRIMARY CARE

(71) Applicant: Boogio, Inc., Kent, WA (US)

(72) Inventors: Giovanni Nino, Issaquah, WA (US); Jose Torres, Jr., Seattle, WA (US)

(73) Assignee: Boogio Inc., Kent, WA (US)

( * ) Notice: Subject to any disclaimer, the term of this patent is extended or adjusted under 35 U.S.C. 154(b) by 0 days.

(21) Appl. No.: 18/821,950

(22) Filed: Aug. 30, 2024

(65) Prior Publication Data

US 2025/0139578 A1      May 1, 2025

Related U.S. Application Data

(63) Continuation of application No. 16/996,489, filed on Aug. 18, 2020, now Pat. No. 12,079,773, which is a continuation of application No. 14/777,364, filed as application No. PCT/US2014/030752 on Mar. 17, 2014, now abandoned.

(Continued)

(51) Int. Cl.
| | |
|---|---|
| *G06Q 10/10* | (2023.01) |
| *G16H 10/20* | (2018.01) |
| *G16H 10/60* | (2018.01) |
| *G16H 20/60* | (2018.01) |
| *G16H 20/70* | (2018.01) |
| *G16H 50/30* | (2018.01) |

(52) U.S. Cl.
CPC ............. *G06Q 10/10* (2013.01); *G16H 10/20* (2018.01); *G16H 10/60* (2018.01); *G16H 20/60* (2018.01); *G16H 20/70* (2018.01); *G16H 50/30* (2018.01)

(58) Field of Classification Search
CPC ......... G16H 40/67; G16H 40/63; G16H 20/30
See application file for complete search history.

(56) References Cited

U.S. PATENT DOCUMENTS

2005/0234742 A1    10/2005  Hodgdon
2009/0069642 A1     3/2009  Gao et al.
(Continued)

FOREIGN PATENT DOCUMENTS

WO      WO-2009138941 A1 *  11/2009   ........... A61B 5/1117
WO      2012/170584 A1    12/2012
WO      2013/012862 A1     1/2013

OTHER PUBLICATIONS

International Search Report and Written Opinion mailed Nov. 10, 2014, issued in corresponding International Application No. PCT/US2014/030752, filed Mar. 17, 2014, 10 pages.

(Continued)

*Primary Examiner* — Joseph D Burgess
(74) *Attorney, Agent, or Firm* — Christensen O'Connor Johnson Kindness PLLC

(57) ABSTRACT

A healthcare and wellness management system, which can be used to collect and analyze data related to a user's health. Using software applications and sensors embedded on a hardware platform, the system collects psychological and physiological data regarding a subject such as mood or stress level, food intake, and vital signs. The system may generate a health parameter based on the collected data. The system may initiate actions based on the gathered data. Multiple users may be ranked relative to one another based on their health parameters.

18 Claims, 13 Drawing Sheets

Related U.S. Application Data

(60)  Provisional application No. 61/800,273, filed on Mar. 15, 2013.

(56)                    References Cited

U.S. PATENT DOCUMENTS

| | | |
|---|---|---|
| 2009/0281393 A1 | 11/2009 | Smith |
| 2010/0111383 A1 | 5/2010 | Boushey et al. |
| 2011/0022332 A1 | 1/2011 | Kailas et al. |
| 2011/0025493 A1 | 2/2011 | Papadopoulos et al. |
| 2013/0095459 A1 | 4/2013 | Tran |
| 2013/0216989 A1 | 8/2013 | Cuthbert |
| 2015/0186602 A1* | 7/2015 | Pipke .................... G16H 40/63 |
| | | 705/3 |

OTHER PUBLICATIONS

Sung, M, et al., "Wearable feedback systems for rehabilitation", Journal of NeuroEngineering and Rehabilitation, 2005;2: 17, Jun. 29, 2005, doi: 10.1186/1743-0003-2-17, 12 pages.
Sun, F-T, et al., "PEAR: Power efficiency through activity recognition (for ECG-based sensing)," 2011 5th International Conference on Pervasive Computing Technologies for Healthcare (PervasiveHealth) and Workshops, Dublin, Ireland, 2011, pp. 115-122.

* cited by examiner

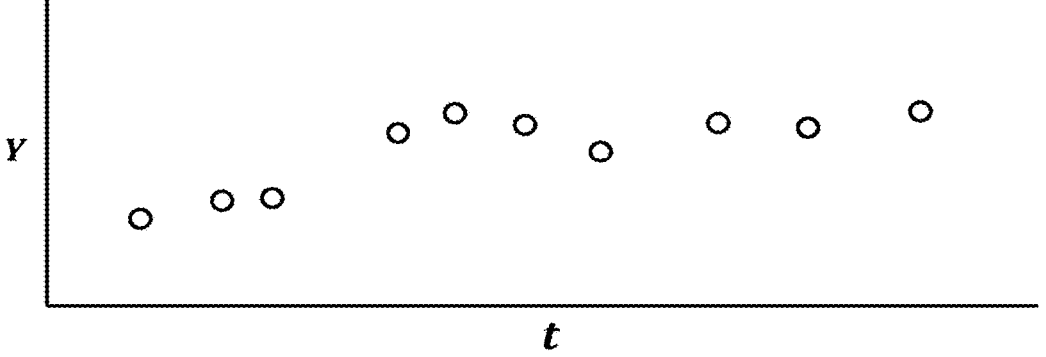
FIG. 8G
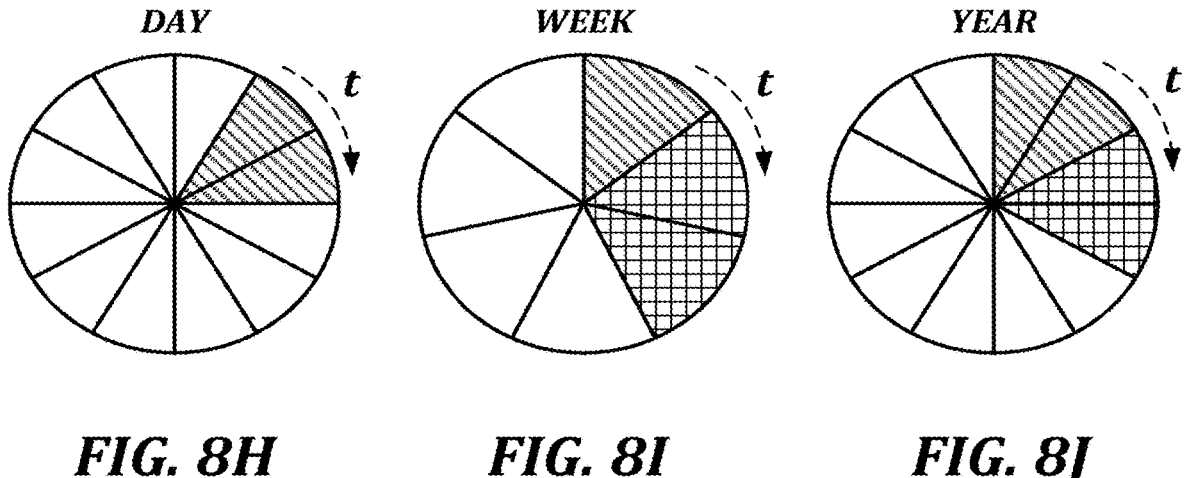
FIG. 8H        FIG. 8I        FIG. 8J

METHOD TO INCREASE EFFICIENCY, COVERAGE, AND QUALITY OF DIRECT PRIMARY CARE

CROSS-REFERENCE TO RELATED APPLICATION APPLICATIONS

This application is a continuation of U.S. patent application Ser. No. 16/996,489, filed Aug. 18, 2020, which is a continuation of U.S. patent application Ser. No. 14/777,364, filed Sep. 15, 2015, which is a National Stage application of International Application No. PCT/US2014/030752, filed Mar. 17, 2014, which claims the benefit of priority of U.S. Provisional Patent Application No. 61/800,273, filed Mar. 15, 2013, the disclosures of which are hereby incorporated by reference herein in their entireties for all purposes.

BACKGROUND

A communication gap exists in the current health care delivery model between a Subject and a provider. This gap is customarily bridged with an office visit where physiological and psychological data regarding the subject is measured and analyzed in person by a medical professional during an office visit. While multiple and more frequent data points and analysis of such data are preferred, it is impractical for a subject to have data sampled regularly under the current model. This limited collection of data points and analysis represents a lost opportunity to aggregate daily physiological and psychological data about the subject, provide a summary of the data to understand underlying issues and trends better, and allow the provider to make more accurate decisions about care based on that data.

There currently exists physiological monitoring technology that gathers limited physiological information about a user, which is presented passively to the user. Current monitoring technologies are narrowly targeted to specific chronic illnesses, sports performance, or weight loss. No action is taken based on the outputs. Data is not fused. This limited information provides limited, if any, indication of overall healthy lifestyle. Moreover, current technology does not gather data about food intake, ingestion of fluids, and emotional state and does not aggregate this data with physiological data. Furthermore, current technology does not detect health events and does not dispatch help automatically for critical events. A solution is needed to monitor multiple health inputs while consuming minimal power and computing resources.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present disclosure, a method of evaluating the health of a subject is provided. The method comprises receiving a first input that is a food data input, receiving a second input obtained during the first time period, and generating a health parameter using both the first input and the second input. The food data input is obtained by analyzing at least one portion of food consumed by the subject during a first time period. The second input is selected from the group consisting of: a mood data input, wherein the mood data input is obtained through active input by the subject during the first time period, a vital sign data input, a biometric data input, a genotype data input, a lifestyle data input, an environment data input, and a biological data input. The health parameter is indicative of the subject's health during the first time period.

In one or more embodiments of the present disclosure, the method may further comprise repeating the steps of the method a plurality of times during subsequent time periods in order to generate a plurality of health parameters, each health parameter being indicative of the subject's health during a specific time period, wherein the plurality of health parameters define a health parameter history of the patient over the time periods. The method may further comprise detecting a health event by: providing a range of potential values for the health parameter that indicates no health event has occurred, and comparing the health parameter during the first time period to the range of values. The method may further comprise providing an alert if a health event is detected. The alert may be provided to a party selected from the group consisting of the subject, a health care provider, a contact designated by the subject, and combinations thereof.

The method may further comprise reporting the health parameter to a party selected from the group consisting of the subject, a health care provider, a contact designated by the subject, a health care information system, an insurance provider, an emergency medical system, a medical facility, and combinations thereof. The food data input may include information selected from the group consisting of a nutrition index, an intake frequency, and combinations thereof. The nutrition index may be generated by analyzing a digital image of the portion of food.

The mood data input may include information regarding a psychological condition of the subject. The psychological condition may include an indication of a mood state selected from the group consisting of anxiety, stress, anger, frustration, happiness, sadness, depression, and combinations thereof. The active input may comprise the subject providing an intensity and a frequency of data input that indicates the mood state. The mood data input may include information regarding a fatigue level or a concentration level of the subject. The active input may comprise testing the subject using a game or a task. The game or the task may be implemented in an electronic device.

The vital sign data input may include information related to a characteristic of the subject selected from the group consisting of heart rate, pulse, blood pressure, blood pressure index, body temperature, breathing, activity, barometric pressure for altimetry, gait, sleep, and combinations thereof. The biometric data input may include information related to a characteristic of the subject selected from the group consisting of age, gender, height, race, metabolic profile, gait, metabolic panel, and combinations thereof.

The genotype data input may include information related to a characteristic of the subject selected from the group consisting of genetic composition, genomic profile, biomarkers, and combinations thereof.

The lifestyle data input may include information related to a characteristic of the subject selected from the group consisting of work, drinking/smoking/eating habits, other habits, activities, hobbies, sports, education, and combinations thereof.

The environmental data input may include information related to a characteristic of the subject selected from the group consisting of geographic information indicative of a geographic position of the subject, weather conditions near the subject, pollution near the subject, economic environmental conditions, social environmental conditions, political environmental conditions, and combinations thereof.

The biological data input may include information related to a characteristic of the subject selected from the group consisting of a skin moisture level, a blood oxygen level, a blood carbon dioxide level, a blood glucose level, a body weight, a body fatty tissue level, an electrocardiogram, an electromyogram, a urine content, a fecal content, an image of the subject, and combinations thereof.

The first input and the second input may include temporal data indicating the time at which the first input and the second input were obtained.

In another aspect, a method of evaluating the health of a subject is provided. The method comprises receiving a first input that is a mood data input, receiving a second input obtained during a first time period, and generating a health parameter using both the first input and the second input. The second input may be selected from the group consisting of: a food data input, a vital sign data input, a biometric data input, a genotype data input, a lifestyle data input, an environment data input, and a biological data input. The mood data input is obtained through active input by the subject during the first time period. The food data input is obtained by analyzing at least one portion of food consumed by the subject during the first time period. The health parameter is indicative of the subject's health during the first time period.

In yet another aspect, a method of evaluating the health of a subject is provided. The method comprises receiving a first input that is a geographic information data input, receiving a second input obtained during a first time period, and generating a health parameter using both the first input and the second input. The health parameter is indicative of the subject's health during the first time period. The geographic information input is indicative of a geographic position of the subject during the first time period. The second input being selected from the group consisting of: a food data input, a mood data input, a vital sign data input, a biometric data input, a genotype data input, a lifestyle data input, an environment data input, and a biological data input. The food data input may be obtained by analyzing at least one portion of food consumed by the subject during the first time period. The mood data input may be obtained through active input by the subject during the first time period.

In another aspect, a method of evaluating the health of a plurality of subjects is provided. The method comprises generating a first health parameter for a first subject and a second health parameter for a second subject and comparing the first health parameter to the second health parameter. The method may use the following steps to generate both the first health parameter and the second health parameter: receiving a first input and a second input, each input obtained during a first time period and generating a health parameter using both the first input and the second input. Each input may be independently selected from the group consisting of: a vital sign data input, a biometric data input, a genotype data input, a lifestyle data input, an environment data input, a biological data input, a food data input, wherein the food data input is obtained by analyzing at least one portion of food consumed by the subject during the first time period, and a mood data input, wherein the mood data input is obtained through active input by the subject during a first time period. The health parameter is indicative of the subject's health during the first time period.

In one or more embodiments of the present disclosure, the method may rank the first health parameter and the second health parameter with regard to the urgency with which the first subject and the second subject require medical attention. The method may generate a third health parameter for a third subject using the above steps and comparing the third health parameter to the first health parameter and the second health parameter.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIGS. 8A-8J are graphical representations of data illustrating different inputs as a function of time in accordance with one or more aspects of the present disclosure;

DETAILED DESCRIPTION

Figure 1:
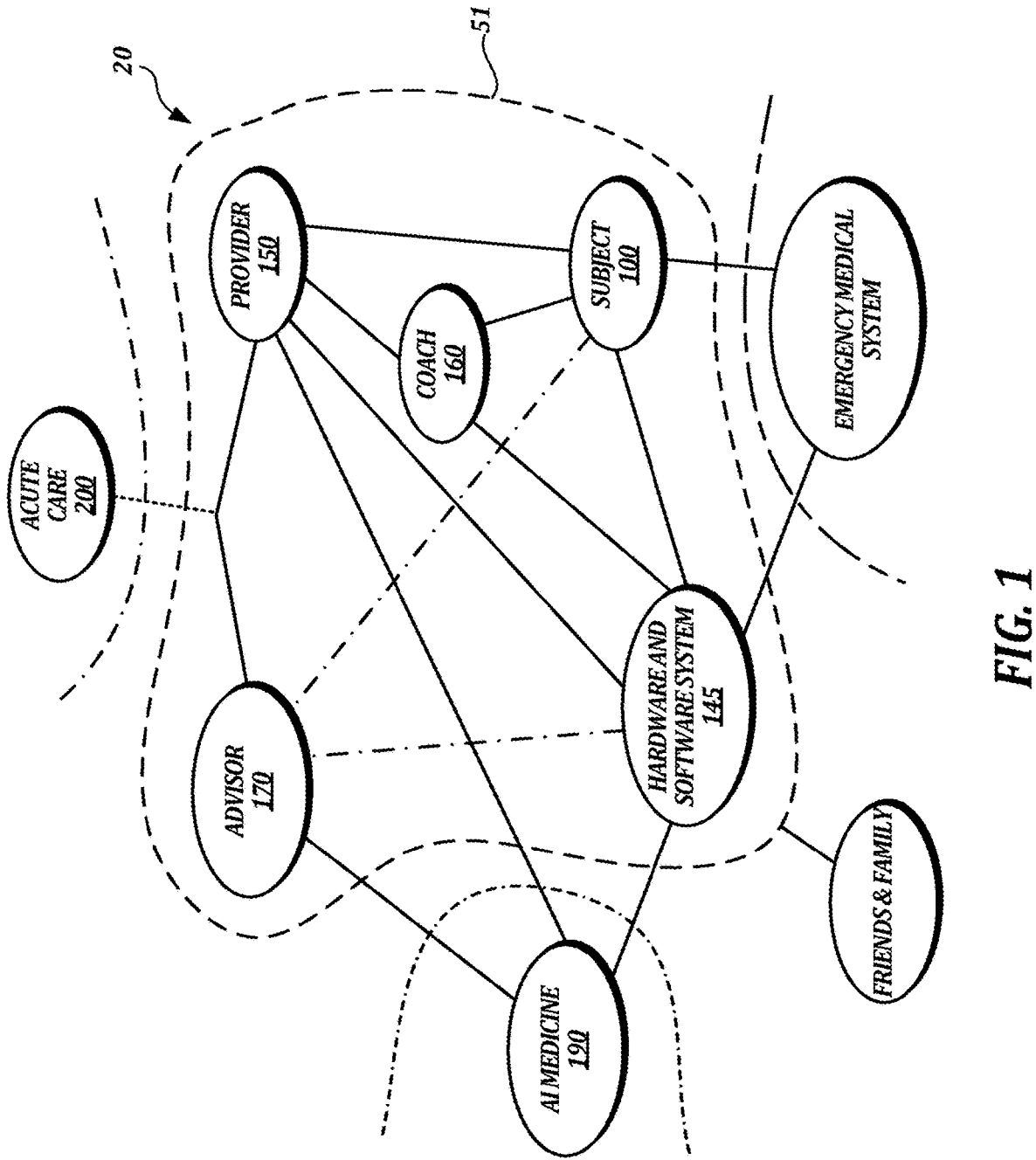
FIG. 1 is a drawing of the primary care health Ecosystem in accordance with one or more embodiments of the present disclosure.

The embodiments of the present disclosure hereinafter overcome the deficiencies of the prior art by using hardware and software to provide for improved assessment of a Subject's health to be determined using both psychological and physiological inputs. Embodiments of the present disclosure may utilize one or more data inputs related to food intake, mood, stress, and body vital signs, among others. A more comprehensive health assessment may be provided by measuring and analyzing body intakes, outputs, vitals, and mood information on a regular and continuous basis and generating outputs based on such information to Subjects and Providers. The embodiments disclosed herein may also reduce the impact and severity of health events by automatically dispatching timely medical help in critical health event situations. Health illiteracy may be reduced by providing relevant/vital metrics of body performance and general wellness. Health costs may be decreased and general wellness may be increased by providing timely feedback regarding a Subject's health status using the provided system. Relevant information about the Subject may be communicated to friends, Providers, Coaches and incremental positive feedback loops may be provided within a positive, socially supportive community. The information gap between people and providers may be reduced. Adverse health changes may be determined and communicated to health care professionals. Such determinations and communications may be performed automatically. Data may be aggregated and made available to Subject and Provider by way of a searchable database of aggregated health data. This may facilitate increased transparency and efficiency during a health assessment and improve the accuracy of a Provider's diagnosis. Data may include data generated or input by both the Subject and the Provider.

As discussed in more detail herein, embodiments of the present disclosure also reduce consumption of computing resources and maximize battery life of the Technology by adjusting the sampling frequency and other processing frequency up or down based on, for example, a Subject's determined overall health. Unnecessary sampling and computations are reduced. Sampling rates are increased when additional data points are useful and decreased when additional data points are not useful. In addition to reducing power consumption and computation resources, adjusting sampling frequency may help to avoid aggregation of data that is not useful, therefore reducing consumed storage resources. While various embodiments are illustrated and described herein, it will be appreciated that changes can be made without departing from the spirit and scope of the disclosure. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Additionally, it will be appreciated that embodiments of the present disclosure may employ any combination of the features described herein.

The following definitions, with reference to numbering in the FIGURES are provided to help clarify certain aspects of the disclosure and should not be construed as limiting.

20 Ecosystem—A health-oriented environment that integrates hardware and software in an open or closed network communicating information related to a Subject 100. The Ecosystem 20 includes subsystems that collect, analyze, and log data related to a Subject 100, and tracks the health condition and wellness of a Subject 100. Ecosystem 20 may include one or more secure and individual digital accounts associated with the Subject 100 or other parties within the Ecosystem 20.

100 Subject—A person receiving services from the Ecosystem 20.

110 Technology—Software and Hardware used to determine health data of a Subject 100. Technology may include physical properties of a Subject.

113 Hardware—Devices capable of collecting, processing and transmitting data, such as wearable computing devices, smart phone, wearable sensor, accelerometer, altimeter, other mobile device, wireless camera, tablet computer, laptop computer, or desktop computer. Hardware 113 is also capable of executing software, such as Software 116.

116 Software—Programs, applications (also referred to as "Apps"), Web sites and protocols that can be executed by hardware, such as the Hardware 113.

120 Data Metrics—Collected data about the Subject 100. This may be received from the Technology 110 or from a network.

123 Collected Software Data—Data collected by Subject inputs and analysis of hardware data, such as, for example, Food, Mood, Profile, and other inputs.

125 Collected Hardware Data—Data collected directly by Hardware, such as Physiological Data, Vital signs, Chemical sensing.

127 Algorithm—A function, such as f(x,y,z,t) or routine implemented by software to analyze, make decisions, and determinations about data such as, but not limited to, Collected Software Data 123 and Collected Hardware Data 125. May be implemented by one or more of the Technology 110, the Decision Making Unit 130, or the Data Metrics 120.

130 Decision Making Unit (DMU)—A system to collect, process, analyze, and/or distribute Data Metrics 120.

133 Health Assessment Algorithm—Analysis, aggregation and correlation of multidimensional and multivariate data to assess the health status condition of a Subject 100. The resulting health status of the Subject 100 may be distributed to the network.

136 Database—A compilation of data, such as data to be processed for storage to a network.

140 Real-Time Transmission—A process for transmission of data at the highest priority allowed by devices and networks, such as a process to send critical health events to Emergency Medical Services (EMS) and/or a Caregiver.

145 Hardware and Software System—Overall hardware and software system that includes Technology 110, Data Metrics 120, DMU 130, Algorithm 127, and may include Database 136 as well as other hardware and software within the Ecosystem 20.

150 Provider—A caregiver such as a medical doctor (MD), Physician Assistant Certified (PAC), or Registered Nurse Practitioner.

160 Coach—A health care or wellness advisor without formal medical training, such as a Personal Trainer, Therapist, or Consultant, that provides guidance to the Subject 100 with advice from a Provider, Advisor, and/or DMU.

170 Advisor—A Medical Doctor who oversees a group of Providers, Coaches, and Subjects with assistance from a DMU and/or Artificial Intelligence Medicine.

180 Critical Assistance—An instance wherein EMS and/or a Caregiver is automatically dispatched by the Data Metrics Algorithms.

190 AI Medicine—Artificial Intelligence Medical advice complied from meta-compilations of medical data that may include Big Data 240.

200 Acute Care—Referral to services rendered by a hospital to provide care beyond the scope of the primary care Ecosystem.

210 Report—An interactive chart, graph, and/or data set to communicate health data such as an Event, trend, recommendation, direction, or advice to hardware devices such as tablets, laptop, Smartphone, wearable computer devices, or servers.

220 Visit—An appointment with a Coach, Provider, or Advisor.

230 Scheduling—A system used to schedule appointments on behalf of a Subject with a Coach, Provider, or Advisor based on priority assigned by the Ranking System Algorithm, Subject, Advisor, Coach, or Provider.

240 Big Data—Meta-compilations of medical data that may exist in public or private databases, e.g., IBM's Watson system. Big Data 240 may be a collection of data sets so large and complex that it becomes difficult to process using on-hand database management tools or traditional data processing applications.

250 Ranking System—Data to be flagged, ranked, processed, and distributed based on Data Metrics.

Embodiments of the disclosure will now be described with reference to the figures. Turning now to FIG. 1, there is shown an example Primary Care Health Ecosystem or "Ecosystem" 20. The Ecosystem 20 includes a Subject 100 (sometimes referred to as "Member"), a Hardware and Software System 145, and a Provider 150. The Subject 100, as described herein, represents a person in most instances. It should be appreciated that the Subject 100 could include animals, such as pets, wild animals, or livestock. The Subject 100 may be a person receiving care and services related to the wellness and health provided in the Ecosystem 20.

The Ecosystem 20 may include a Coach 160, an Advisor 170, and Friends (not shown). In some embodiments, the Advisor 170 is a medical doctor that manages one or more Providers 150 and can advise on cases requiring a second opinion. The Advisor 170 may access data about the Subject 100, query Big Data 240 for advice, or access Data Metrics 120. Other sub-elements or "parties" may be included in the Ecosystem 20 such as family, peers, caretakers, emergency management services, providers, payers, private corporations, government programs, and researchers.

The sub-elements of the Ecosystem 20 may be connected to one another, as shown in FIG. 1, for example. In addition, sub-elements of the Ecosystem 20 may be connected to other systems, such as Emergency Medical Services (EMS), AI Medicine 190, and Friends, and Family. Some sub-elements may be separated by a data protection boundary 51, which limits the data that may be transferred or accessed by certain parties included or excluded from the Ecosystem 20. In some embodiments, Hospitals, EMS, AI Medicine, and Friends/Family on the outside of the data protection boundary 51 are referred to as being "outside" of the Ecosystem 20 and treated as third parties in regard to accessing data of the Ecosystem 20.

Figures 9A, 9B:
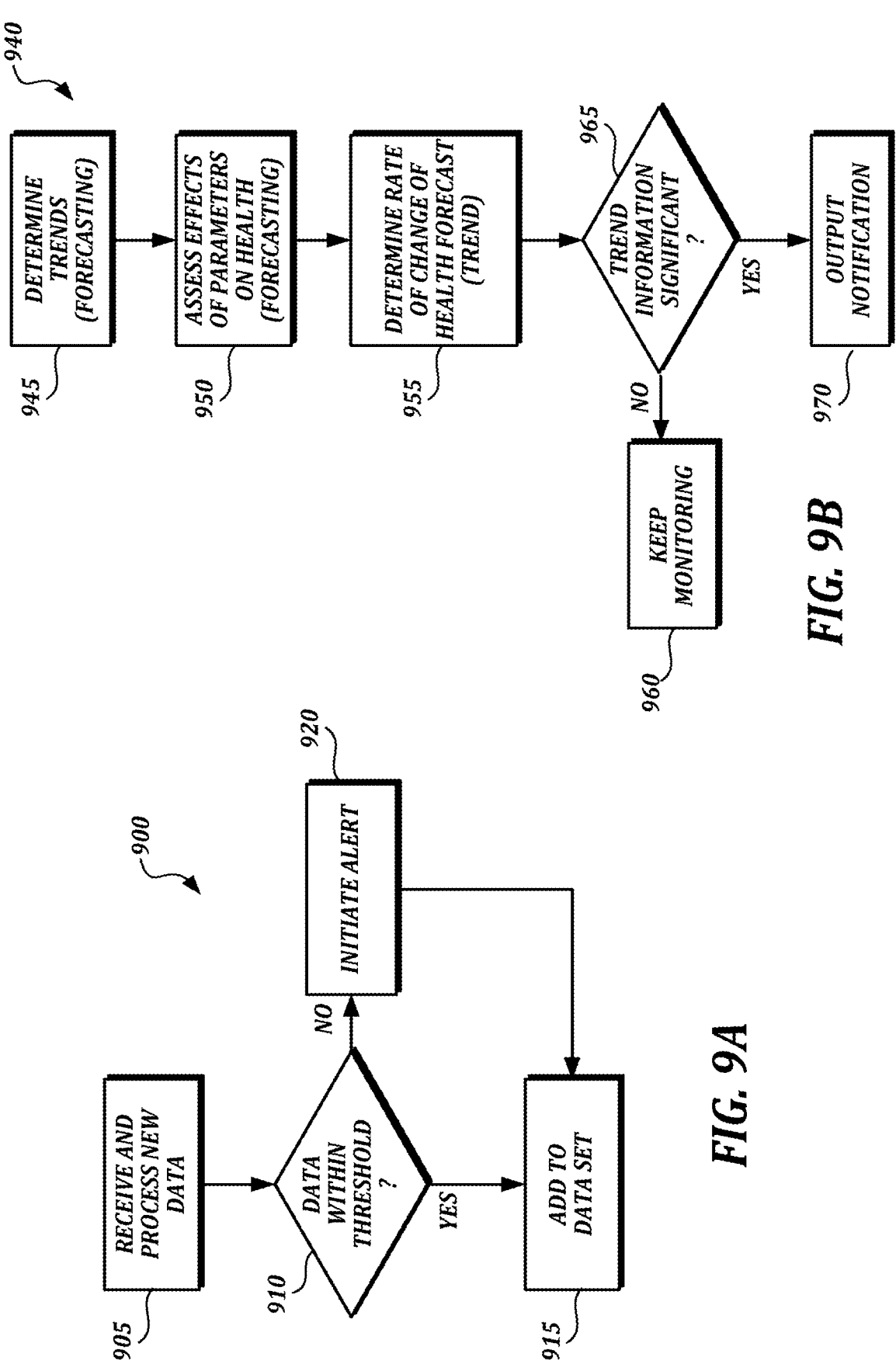
FIGS. 9A and 9B are health assessment flowcharts in accordance with one or more aspects of the present disclosure.

In certain embodiments disclosed herein, such as, for example, the embodiments shown in FIGS. 9A and 9B, if a life-threatening situation is determined, a communication (also referred to as "feedback") is provided to the Subject 100 or another party. For example, communications or "distress signals" may be issued by the Hardware and Software System 145 to an EMS for an appropriate response. In some embodiments, the distress signal will be sent to a local EMS based on a location of the Subject 100, as determined by Global Positioning System (GPS) coordinates. In addition, or alternatively, communications regarding a Subject's health state may be issued to defined contact persons. Communications may be sent using multiple formats such as, but not limited to, text, voice, or video messages. Communications may be encrypted to enhance security and protect identity. Data may be communicated or transferred between sub-elements and between subsystems of sub-elements, such as the Hardware and Software System 145.

Figure 2:
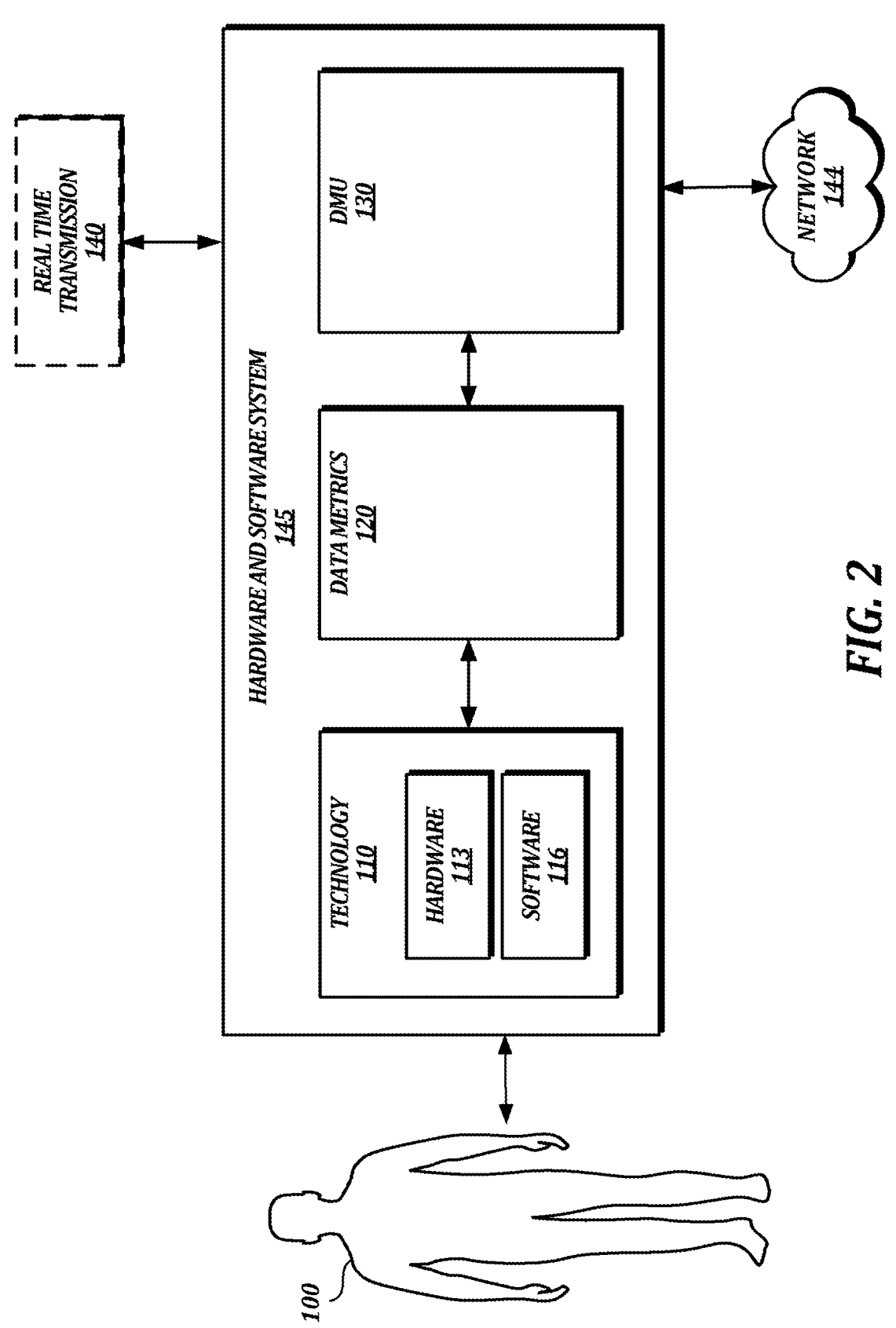
FIG. 2 is a block diagram showing a system architecture used in the Ecosystem in accordance with one or more aspects of the present disclosure.

Referring now to FIG. 2, a block diagram of an embodiment of a Hardware and Software System 145 ("System") suitable for use in Ecosystem 20 is shown. The System 145 includes Technology 110 and Data Metrics 120 and may include DMU 130. It will be understood that the subsystems of System 145 may be embodied as separate computing devices or subsystems or may be combined with one another and/or included in one or more other systems.

The Technology 110 includes the Hardware 113 and Software 116. The Subject 100 interfaces with the Technology 110 such that the Technology 110 may sense various inputs associated with the Subject 100. The Hardware 113 comprises one or more input devices, such as a sensor. The Hardware 113 can be made of currently known or later-developed materials. Hardware 113 may include, for example, one or more of wearable sensors, embedded sensors, and environmental sensors. The Hardware 113 may include, for example, various "smart devices" or sensors that are worn, such as watches, bracelets, jewelry, clothing, underwear, socks, hats, shoes, belts, glasses, and rings. Hardware 113 may be custom fitted, produced, or made specifically based on the shape, size, and sensitivity of the Subject 100. The Hardware 113 may be customized, for example, using measurements of a Subject 100 captured via 3D scans or a particularly shaped person, in general, and used as a model for production. Hardware 113, for example, may be readjusted and reconfigured over time to adapt to the changing body contours of the Subject 100. The Hardware 113, for example, may include sensors that can be applied directly to the body in the form of stickers, patches, temporary tattoos, and contact lenses or sensors that may be embedded in the body, such as implants placed directly under the skin, attached to the top of the skin, in the car, digested, surgically implanted on organs or inhaled through pulmonary aspiration. The Hardware 113, for example, may receive or provide data that may be used to determine, for example, vital sign data, biometric data, genotype, gait analysis, position of the body relative to the ground (altimeter), lifestyle data, environmental data, biological data or metabolic data about the Subject 100. The Hardware 113 may use inputs from a plurality of sensors to derive an input. It will be appreciated that some inputs require various levels of processing in order for a particular parameter to be determined, and such processing may be performed by the Hardware 113. In addition, the Hardware 113 may transmit data to other devices or actors included in the System 145, Ecosystem 20 or outside of the Ecosystem 20. Accordingly, it will be appreciated that the Hardware 113, Data Metrics 120, and Decision Making Unit 130 may include one or more appropriate communication modules. In some embodiments, the inputs provided by the Hardware 113 correspond to physical properties of the Subject 100. In some embodiments, the inputs provided to the Hardware relate to health data, food intake and consumption, or the psychological or mental status of the Subject 100.

The Hardware 113 may sample data at various sampling rates or frequencies. In certain embodiments, the sampling frequency for some or all inputs may be adjusted up or down. Such adjustment may occur in real time. In certain embodiments, the sampling frequencies are adjusted up or down depending on the level of detail that is desired about a particular input. The desired level of detail may be determined by the Algorithms, Subject, Provider, Advisor, Coach, or AI Medicine, and the data is then transmitted to a wireless network for further analysis. Reducing sampling frequency may drastically reduce the processing load and provide for reduced power consumption. Reducing power consumption is an important concern as one or more of the Technology 110, Hardware 113, and Data Metrics 120 may be wearable and portable and, therefore, powered by a portable power supply. Reducing power consumption may also reduce the heat generated by these devices, making them easier to use and more comfortable.

The Software 116 includes applications and algorithms. Software 116 may be implemented in a smart phone, tablet, or personal computer, in the cloud, on a wearable device, or other computing or processing device. The Software 116 may include logs, journals, tables, games, recordings, communications, SMS messages, Web sites, charts, interactive tools, social networks, VOIP (Voice Over Internet Protocol), e-mails, and videos.

The Data Metrics 120 includes hardware and software. Data Metrics 120 may compile data collected by the Technology 110, and Data Metrics 120 may determine and receive inputs. Data Metrics 120 may receive or provide data regarding the food and drink consumption of the Subject 100 as well as physiological data, such as blood pressure, heart rate, temperature, as well as other parameters, such as location, as determined by a GPS, and environmental factors, such as weather, elevation, time of day, and time. In some embodiments, Data Metrics 120 obtains such information by accessing a network 144, such as the Internet, for example, and without limitation.

The inventors of the present application have found that food and mood or "stress" parameters complement physiological data of the Subject 100 to determine an overall health of the Subject 100. Accordingly, certain embodiments of the present application use a food intake and a psychological state (also referred to as "stress") of the Subject 100 as inputs. Various tools implemented in Technology 110 or Data Metrics may be used to capture and assess a person's food intake and mood. Food refers to hardware and/or software that provides data or an input corresponding to a quantity of food and drink consumed by the Subject 100. Mood refers to hardware and/or software that provides data or an input corresponding to a mood of the Subject 100.

Figure 11:
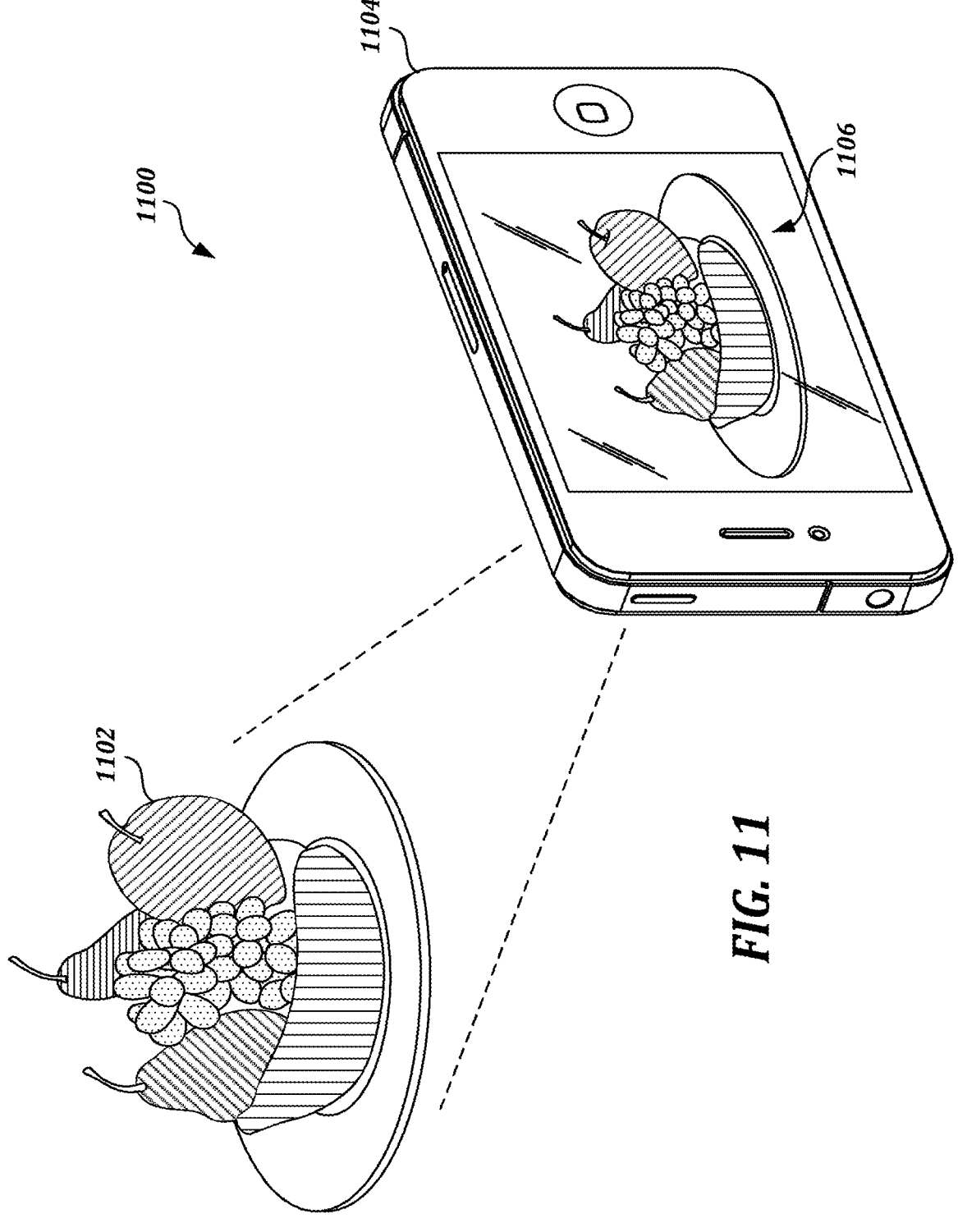
FIG. 11 is an illustration of an exemplary food input tool suitable for use with one or more aspects of the present disclosure.

Referring now to FIG. 11, an example embodiment of food tool 1100 is shown. Food tool 1100 is suitable for use with the System 145. The food tool 1100 includes software executed by a computing device, such as a smart phone 1104. The food tool 1100 is used to determine a nutritional content of a portion of food 1102 that may be eaten by the Subject 100. The food tool 1100 uses, for example, a Web-enabled digital camera included in the smart phone 1104 to generate an image 1106 of the portion of food 1102. The food tool 1100 performs image processing on the generated image 1106 to estimate nutritional value of the portion of food 1102. The food tool 1100 may, for example and without limitation, determine the nutritional information of the portion of food 1102 based on colors, size, and shape of the food included in the generated image 1106.

In some embodiments, a nutrition index is generated by analyzing a digital image of the portion of food. In some embodiments, the identity of a portion of food is determined by a method comprising: obtaining a digital image of the portion of food; determining the type of food by comparing the digital image to a database of known food types, wherein the determination may rely on color, shape, texture, or other detectable characteristics of the food portion that can be conveyed by the digital image; prompting a user to verify the determined identity of the food; prompting the user to modify the determined identity of the food along with additional characteristics of the food (e.g., amount, specific food type, etc.); and determining the composition of the portion of food, including type of food and nutritional content (e.g., calories, fat, protein, etc.). As with other inputs, the nutritional information may be logged over time for broader analysis. It will be appreciated that the processing can be performed locally by the Technology 110, the smart phone 1104, Data Metrics 120, or over a central computing unit over the Internet where data is aggregated to other metrics/data sets. In some embodiments, an electromagnetic scattering sensor (not shown) may be included in the smart phone 1104 and may be used to generate a depth image of the portion of food 1102. The depth image may be used to aid in determining the identity of the portion of food, a nutritional index, or other nutritional information.

Mood tools capable of providing or receiving mood inputs regarding a Subject may be implemented in various ways, such as using a software application executed by computing devices such as a smart phone or a tablet. For example, the Subject 100 may input how he or she feels at one or more times throughout the day by selecting an indicator that best reflects his or her mood such as happy, sad, stressed, or angry. The Subject 100 may be prompted for such an input at times corresponding to various sampling frequencies as discussed above. In some embodiments, a user of a mood tool selects from a plurality of face images that represent different moods. For example, the Subject 100 selects a happy face to indicate the Subject 100 is feeling happy. For example, the Technology 110 may use an optical sensor, such as a camera, to generate an image of a facial expression of the Subject 100 and determine the Subject's mood based on the image of the facial expression. The System 145 may use a digital camera, such as a camera found on a smart phone, for example, to generate the image. In some embodiments, electromagnetic scattering sensors may be used to generate a depth image of the facial expression of the Subject 100, which may be used to determine the mood of the Subject 100.

Figures 12A, 12B:
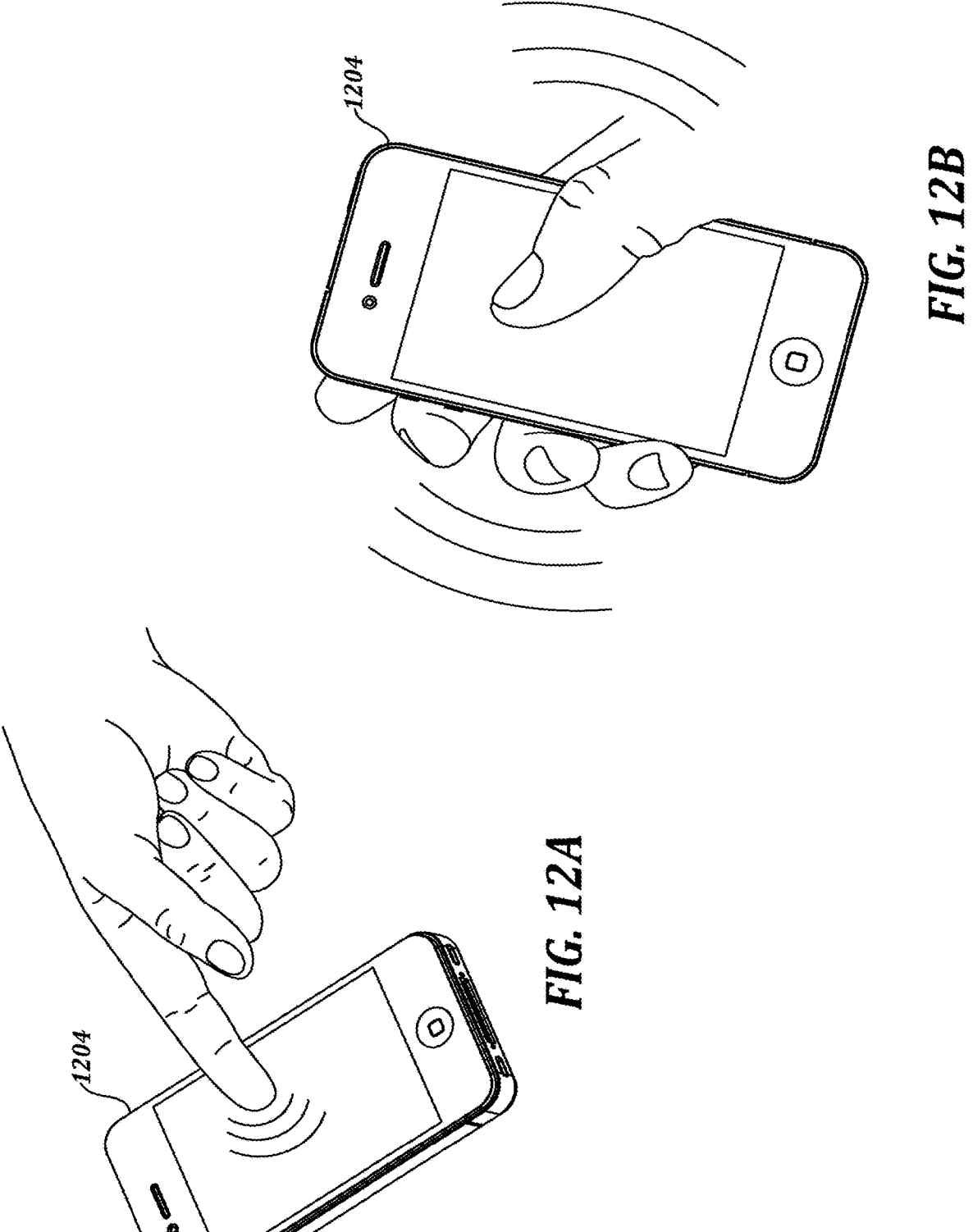
FIGS. 12A and 12B are illustrations of exemplary mood input tools suitable for use with one or more aspects of the present disclosure.

Referring now to FIGS. 12A and 12B, embodiments of a mood application implemented in a smart phone 1204 are shown. In the embodiment shown in FIG. 12A, a mood or stress level is determined by a user based on user inputs (taps or touches) to a touch screen of the smartphone 1204. In the embodiment shown in FIG. 12B, a mood or stress level is determined based on a user shaking the device. Levels of stress, anxiety, and other emotional states of the Subject 100 may be determined based on the frequency and/or intensity of the inputs. For example, if the Subject 100 is feeling anger or stress, he or she may shake or tap the smart phone 1204 more frequently and/or with greater intensity than if the Subject 100 is feeling happy or relaxed. In some embodiments, input intensity, frequency, or a determined mood is transmitted to a central computing unit to be aggregated to other metrics/data sets. It will be appreciated that the examples included in this disclosure, such as FIGS. 12A and 12B, are non-limiting and inputs, such as food and mood, may be determined using other currently available or later developed technology. For example, smart phone or computing device sensors (e.g., accelerometers, touch screens, microphones, or a force pressure sensor) may be used to determine mood and food inputs. In one embodiment, the Subject's mood is conveyed to a computing device, such as a smart phone or table, by a method that includes providing a sensor configured to receive physical input from the user (e.g., by shaking or tapping the sensor); sensing a physical motion of the user using the sensor configured to receive physical input; and correlating the sensed physical motion with a particular mental state (e.g., happy, sad, stressed). In some embodiments, a mood data input includes information regarding a fatigue level or a concentration level of the Subject 100. In some embodiments, the active input comprises testing the Subject using a game or a task. In one embodiment, the game or the task is implemented in an electronic device.

TABLE 1 shows examples of various parameters and inputs that may be provided or received by the System 145.

TABLE 1

DATA METRIC HEALTH PARAMETERS

| Input/Data entry[1] | Description |
| --- | --- |
| Food | Nutrition index |
| | Intake frequency |
| Mood | Mood state |
| (psychological) | Fatigue/Concentration levels may be determined |
| | using a game or app to assess, record, and track |
| | these inputs |
| | Gait |
| Vitals | Heart rate and/or pulse |
| | Blood pressure/blood pressure index |
| | Body temperature |
| | Breathing |
| | Activity/Sleep pattern |
| | Position relative to the ground (altimetry) |
| Profile | Biometrics (e.g., age, gender, height, race, |
| | metabolic profile, metabolic panel, gait) |
| | Genotype (e.g., genetic composition, genomic |
| | profile, biomarkers) |
| | Lifestyle (e.g., work, hours worked, |
| | drinking/smoking/eating habits, other habits, |
| | activities, hobbies, sports, education) |
| Environment | GPS (e.g., Geolocation or "Geotag") |
| | Weather (e.g., temperature, humidity, rain, snow, |
| | wind, UV index) |
| | Pollution (e.g., noise, pollen, water, air, chemicals) |
| | Social, political, and economical environment (news) |
| Other Biological | Skin moisture |
| Signals and | $O_2/CO_2$ content |
| Inputs | Glucose |
| | Weight |
| | Body Mass Index |
| | ECG/EKG/EMG |
| | Urinanalysis from smart toilets or home sensors |
| | Fecal analysis from smart toilets or home sensors |
| | Daily image of patient from smart mirrors or cameras |
| | at home |
| | Gait |

[1]The signals and responses may have associated spatial, geolocation, or time coordinates.

Geolocation may include the identification of a real-world geographic location of a person. Geolocation may be used with the embodiments disclosed herein to determine various environmental factors, such as, but not limited to, home, work, travel, inside, eating, sleeping, or outside. In some embodiments, geolocation is used to determine food or pollution inputs or identify if the Subject is visiting a particular fast food restaurant.

Referring back to FIG. 2, the DMU 130 includes hardware and software. In some embodiments, the DMU 130 includes software that determines an overall health parameter indicative of the overall health of the Subject 100 based on the inputted data from the Technology 110. The DMU 130 may use data from the collected processed metrics and parameters, such as those included in TABLE 1, and may store processed data in a local or remote Database 136 for further long-term analysis. In some embodiments, the DMU 130 sends data to a device configured with a Ranking System 250 for further analysis and action. In some embodiments, the DMU 130 causes a Report 210 to be generated and provided to the Subject 100. The gathered data can be locally processed and the result transmitted to a server, a portable device, or both.

In some embodiments, the DMU uses a data fusion algorithm to analyze and interpret the collected data. Accordingly, biological, physiological, emotional, and environmental information may be gathered from different types of sensors, and an overall health parameter may be calculated based on the inputs. In addition, the System may perform a risk evaluation process to identify possible health risk events. Some examples of these risks are shown in TABLE 2, and may be based on different metrics and defined threshold values. For example, a fall can be inferred for a Subject by combining different data such as sudden acceleration, variation in pulse rate, time and duration of the event, geolocation (house, mountains, street, other), and noise from a microphone. In some embodiments, once a risk event has been identified, a confirmation communication may be directed to the Subject to assess whether the identified risk is a false positive or not. If confirmation is obtained by the Subject, the System may automatically contact the closest EMS service based on received geolocation information of the Subject. In some embodiments, messages (reporting tools) in different formats, e.g., voice, data, or video, may be automatically sent to defined persons. In addition, collected information may be aggregated to other metrics/data sets. The recipients and method and type of data communicated may be determined by the System and based on the determination of a particular event or an associated severity level such as:

"Normal"—Data, such as vital signs, can be transmitted back to the Subject in a meaningful way that promotes healthy living;

"Abnormal"—Data such as vital signs can be transmitted to a party specified by the Subject (e.g., self, partner/ spouse, family, doctor, others);

"Critical"—Data such as vital signs can be transmitted to EMS for immediate life support services; and "Lifestyle"—Daily activity points are scored using the aggregated data collected by the sensors. In some embodiments, such data can be shared with family and friends to encourage general wellness in the network (social media) without revealing personal health information.

TABLE 2 shows examples of measured parameters or "inputs" that may be used by the System 145 to determine or recognize a particular event or behavior. The measured parameters may be used alone or in combination with other measured parameters.

TABLE 2

| ID | Event Recognition/ Behavior | Measured Parameter(s) |
| --- | --- | --- |
| 1 | Dehydration | Skin moisture, temp, GPS, time |
| 2 | Edema (water retention) | Skin moisture, swelling, pressure/strain, time, temperature, blood pressure |
| 3 | Fever | Temperature, skin moisture, time, GPS coordinates. GPS coordinates may be local or general |
| 4 | Hypothermia | Temperature, GPS, time |
| 5 | Fall | Accelerometer, heart rate, time, microphone, GPS, barometric pressure for altimetry |
| 6 | Sleep pattern | Accelerometer, temperature, heart rate, microphone, time, GPS, barometric pressure for altimetry, gait |
| 7 | Hypo/hyper-tension | Blood pressure, heart rate, time |
| 8 | Faint | Accelerometer, blood pressure, $O_2/CO_2$ in blood, heart rate, time, barometric pressure for altimetry |
| 9 | Stress/ anxiety | Heart rate, blood pressure, breathing, microphone, food and mood, time, GPS, gait |
| 10 | Depression | Sleep (6), stress (9), Food and Mood, accelerometer, time, microphone, gait |
| 11 | Heart attack | Heart rate, blood pressure, ECG, $O_2/CO_2$ in blood, time, barometric pressure for altimetry |
| 12 | Stroke | Blood pressure, accelerometer, hearth rate, time, gait |
| 13 | Hemorrhage | Blood pressure, time, temperature, heart rate |
| 14 | Sleep apnea | Microphone, accelerometer, heart rate, time, GPS |
| 15 | Body fat/ mass index | Ultrasonic acoustic response |

TABLE 2-continued

| ID | Event Recognition/ Behavior | Measured Parameter(s) |
|----|------------------------------|------------------------|
| 16 | Other-Glucose | Glucose, pH from sweat analysis |
| 17 | Weight gain | Ultrasonic acoustic response, weight from external devices |

Figure 6:
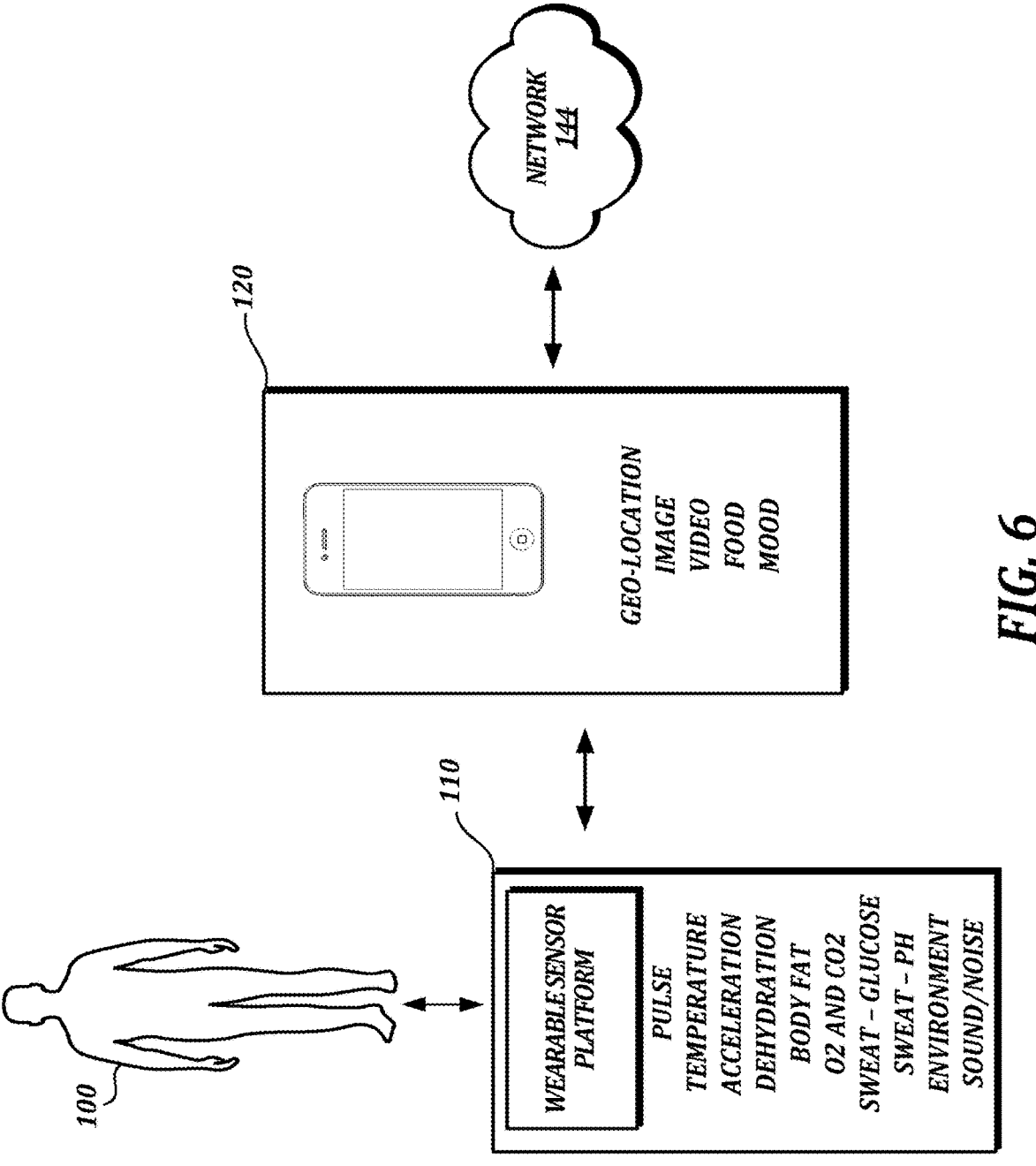
FIG. 6 is a block diagram showing subsystems of the Ecosystem in accordance with one or more aspects of the present disclosure.

Referring now to FIG. 6, an example of Technology 110 and Data Metrics 120 is shown. Technology 110 includes a wearable sensor platform that senses one or more of physical properties of pulse, temperature, acceleration, gait, dehydration, body fat, $O_2$, $CO_2$, Sweat-Glucose, Sweat-pH, Environment, barometric pressure for altimetry, and Sound/ Noise. Data Metrics 120 includes a smart phone connected to network 144. Data Metrics 120 receives or provides Geo-Location, image, food, and mood inputs.

A Health Assessment Algorithm 133 may be used to determine an overall health condition or "health status" of the Subject 100. Health data of the Subject 100 data may be analyzed periodically or in response to a request from a Provider, Advisor, or Coach. In some embodiments, the frequency of data analysis and/data collection depends on the overall health condition of the Subject 100. A health status of the Subject 100 may be defined based on the Subject historical data and profile information. In some embodiments, the data gathered as a function of space and time (f(x,y,z,t)) is analyzed to obtain correlations between different parameters and health states and to determine or infer a Subject health trend. In such embodiments, a multivariate analysis may be performed where one or more inputs, logged in time and space, will be analyzed. Correlations between different parameters will be used to obtain an accurate representation of the Subject's health status. Based on the gathered data, short term, midterm, and longterm forecasts will be determined for relevant health performance parameters using multivariable regressions. The variation of the determined forecast trends (increase, decrease, stable) or metrics will be used as an indication of health behavior. If the health status is determined to be a threshold level, for example, "critical," then the Subject information is sent to the Ranking Algorithm 250 shown in FIGS. 3 and 4. The Ranking Algorithm 250 schedules an appointment with a Provider 150. In some embodiments, the System 145 reports the health parameter to a party selected from the group consisting of the Subject, a health care provider, a contact designated by the Subject, a health care information system, an insurance provider, an emergency medical system, a medical facility, and combinations thereof.

Figure 3:
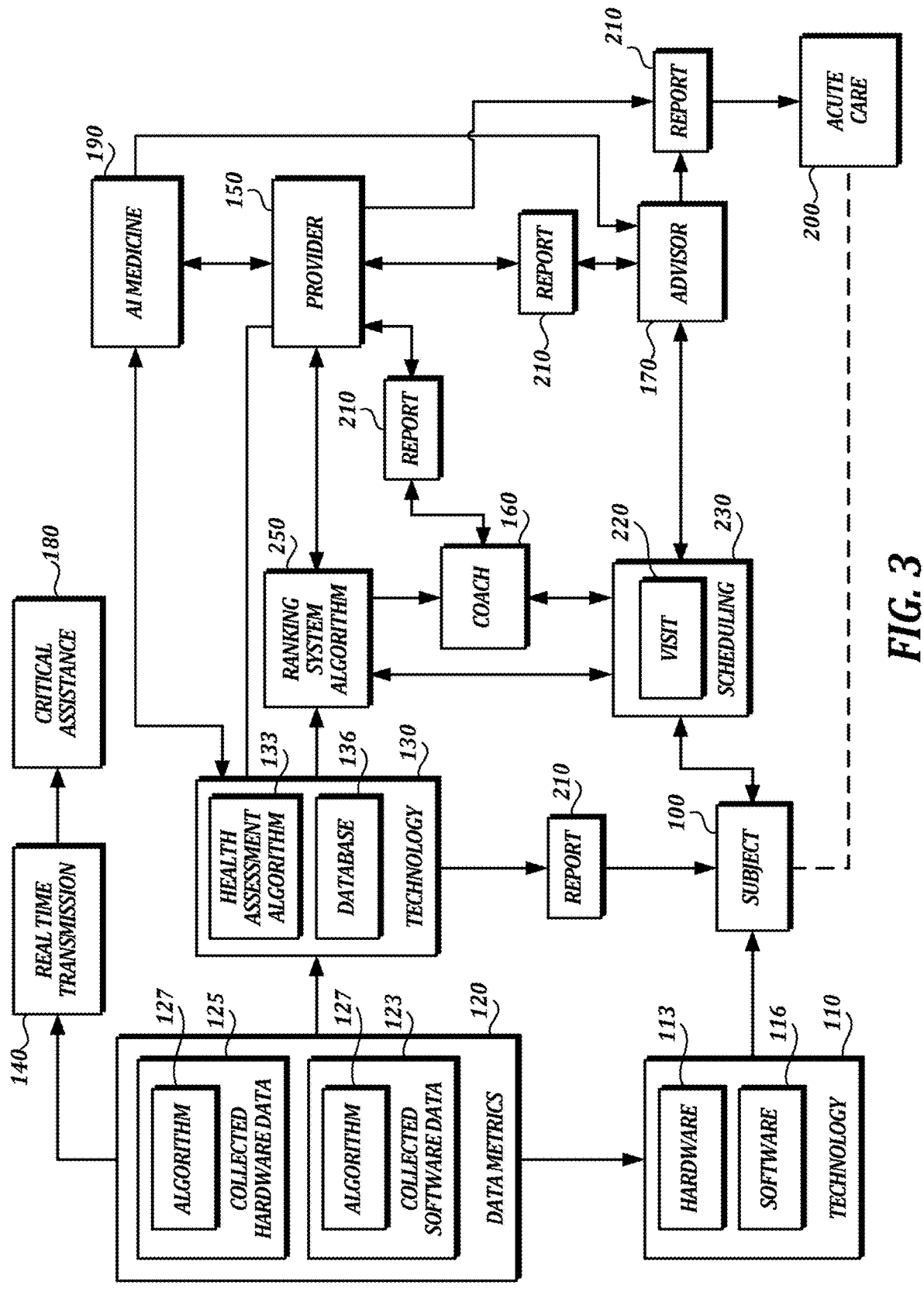
FIG. 3 is a block diagram illustrating data communication throughout the system architecture in accordance with one or more aspects of the present disclosure.

Referring now to FIG. 3, a block diagram is provided that shows an example of the flow of data within the Ecosystem 20. FIG. 3 may be used with the System 145, for example. In certain embodiments, the Subject 100 may input data into the Technology 110 that may be analyzed either by, for example, the Technology 110 or the Data Metrics 120. For example, the Subject 100 may manually input data related to his or her overall physical and mental condition. The Subject 100 may be an active participant in the overall quality of care and the type of services and treatments received relating to their health and wellbeing.

Referring back to FIG. 3, a Report 210 may be generated or caused to be generated by the Decision Making Unit 130, for example. The Report 210 may include logs, journals, tables, games, recordings, communications, SMS message, Web sites, charts, interactive tools, social networks, VOIP, e-mails, and videos, for example and without limitation. Periodic reports are issued to the Subject summarizing different health parameters, their correlation as a function of time as well as overall health performance. For example, the data can be presented in multidimensional arrays to correlate different health responses as a function of time, events, position, variation in gait over time, Mood, Food, and so on such as shown in FIGS. 7 and 8. Data can be accessed by the Subject 100 and health Provider 150.

Figure 7A:
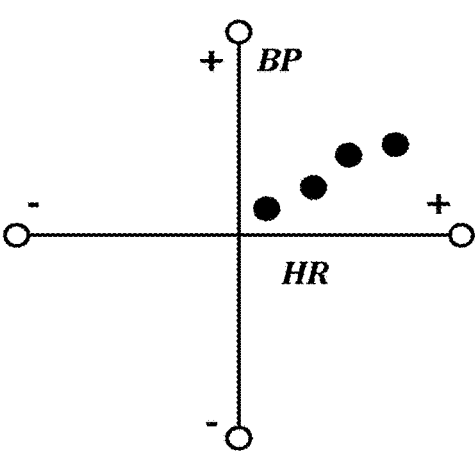
FIGS. 7A-7C are drawings of exemplary graphical representations of data in accordance with one or more aspects of the present disclosure.
Figure 7B:
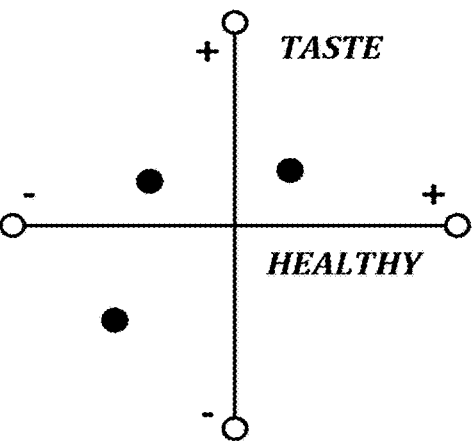
Figure 7C:
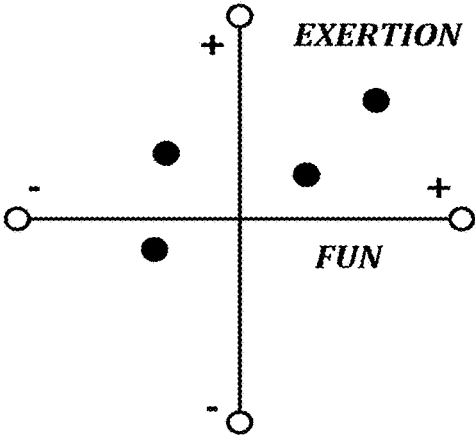

Referring to FIGS. 7A-7C, examples of inputs are shown. Such inputs may be provided to the Subject 100 as feedback or reports or provided to other parties or sub-elements of the Ecosystem 20. FIG. 7A shows vitals inputs related to blood pressure and heart rate. FIG. 7B shows food inputs related to health and taste. FIG. 7C shows activity inputs related to perceived exertion and fun. It should be appreciated that these examples may be displayed using a smart phone or other electronic device or may be printed out as a paper pamphlet, for example.

Figures 8A, 8B, 8C, 8D, 8E, 8F:
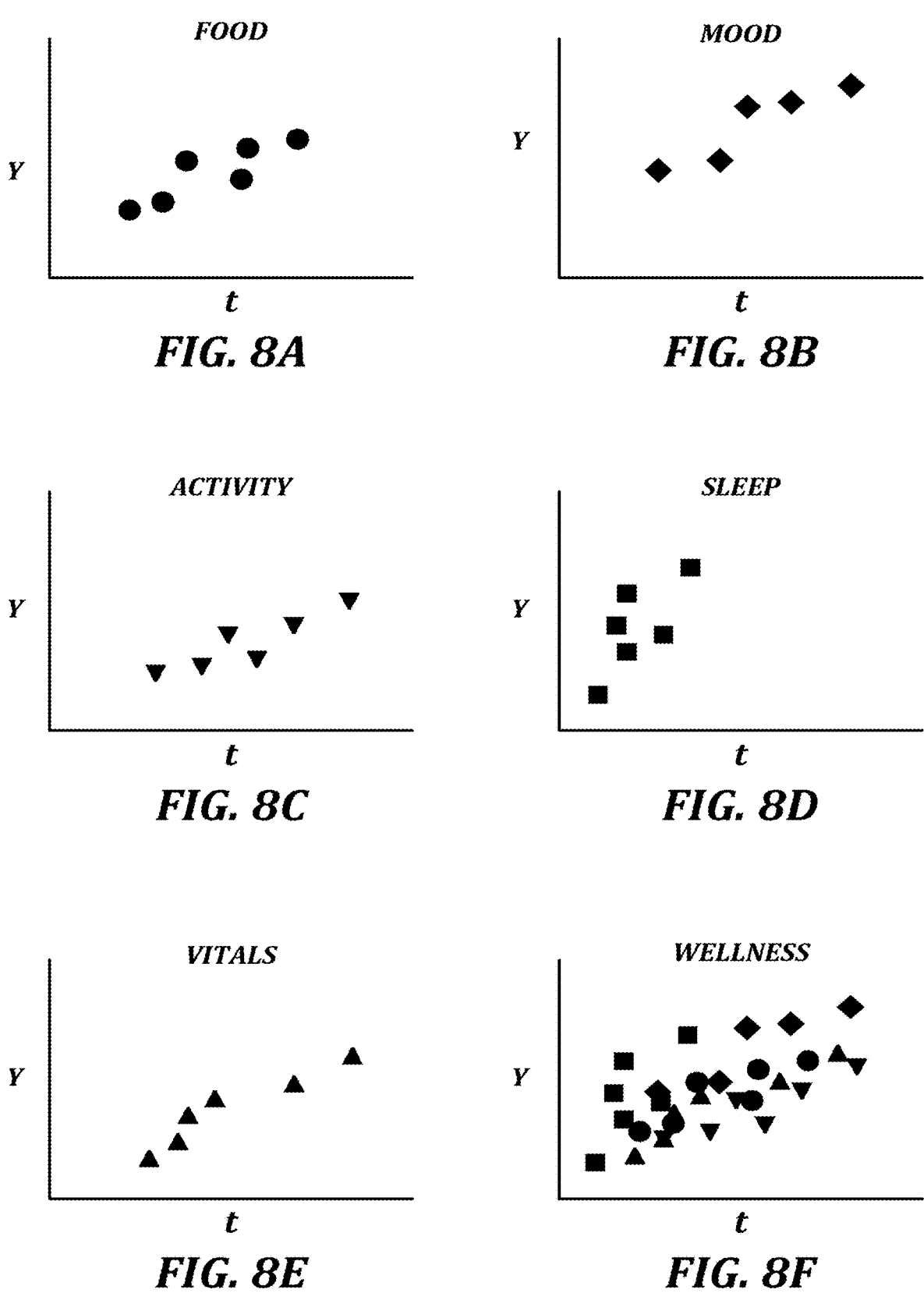

Referring to FIGS. 8A-8J, examples of inputs are shown for particular times or time periods. Such inputs may be provided to the Subject 100 as feedback or reports or provided to other parties or sub-elements of the Ecosystem 20. FIG. 8A shows food inputs over time. Food inputs, for example, may be taste, consumption or nutritional quality or other food-related parameters. FIG. 8B shows mood inputs over time. FIG. 8C shows activity inputs over time. Activity inputs may be, for example, calories, perceived exertion, among others. FIG. 8D shows sleep inputs over time. Sleep inputs may be related to, for example, sleep quality or quantity in hours. FIG. 8E shows vitals inputs over time. The time axis in the preceding figures may correspond to a time or may correspond to average inputs over a particular time period. FIG. 8F shows wellness inputs over time. FIG. 8G shows a health parameter over time. FIGS. 8H, 8I, and 8J show a health parameter, such as, for example, an overall health score over days, weeks, and months, respectively. The health parameter may be color coded using colors that provide feedback. Such scores may be obtained from data storage included within or accessible to System 145. These examples may be presented, for example and without limitation, using a smart phone display, other electronic device, or may be printed.

Referring back to FIG. 3, Visit 220 can be in person at an office or at home, a phone call, an e-mail, a text message, a VOIP, or a video conference. The goal is to focus and schedule different types of visits based on the type of consultation. Visits are to be encouraged to help detect problems in a Subject's health early before more serious adverse effects can take hold. This helps keep the system efficient and cost effective by being focused on the front loading of care.

The Provider 150 may be a licensed medical professional such as a Physician Assistant Certified, Registered Nurse Practitioner, or a Medical Doctor. The main focus of the Provider 150 is to be the primary contact point for the Subject and to engage and manage the entire patient panel actively on a continuous basis. A Coach 160 can be a licensed medical professional such as a Personal Trainer, Therapist, or Consultant that provides guidance to the Subject with advice and in alignment with a Provider, Advisor, and/or DMU. The Focus of the Coach is to help assist a Subject with lifestyle advice, care, mentorship, coping mechanisms, and treatment plans. An Advisor 170 is Medical Doctor who oversees a group of Providers, Coaches, and Subjects with assistance from a DMU and/or AI Medicine.

The primary role of the MD is to manage the entire group of providers, research and compile new findings based on the compiled data, and report findings in the system for further research and study. This helps improve algorithms such as the DMU and ranking system. The MD acts as a bridge between the data and the Subjects as both a provider and research scientist.

AI Medicine 190 refers to Artificial Intelligence Medical advice compiled from Big Data. As used herein, "Big Data" refers to a collection of data sets so large and complex that it becomes difficult to process using on-hand database management tools or traditional data processing applications. Advisors and Providers can interface with this system with logs, journals, tables, Web sites, charts, and interactive tools. AI medicine is used as a tool for additional recommendations. AI will be used to perform an intensive health analysis of the Subject based on the collected data and relevant population data (region, gender, age, race, work type, life style, genotype, health condition, etc.) to find sources of problems and advise best treatment options in the case of illness. This analysis can be performed periodically or by request from the Provider or MD Advisor.

The Subject's networks or panel data can be studied periodically or by request from the Provider or MD Advisor to analyze overall panel health performance with the aim to identify latent or possible health risks correlated or associated with food quality, environmental conditions, geography, season, and any other socio-political factors. Once a risk has been identified, providers, MD advisors, or any other qualified and authorized personnel will provide advice on how to reduce, mitigate, or eliminate the identified risk from the community. Acute Care 200 is care delivered outside the network and beyond the scope of the primary care model. It is often a referral to a hospital or urgent care clinic.

In some embodiments, the System 145 causes actions to occur on behalf of the Subject 100. Such actions may be implemented automatically. The initiated actions may include sending a notification directly to the Subject 100, scheduling an appointment with the Provider 150, sending a report, or contacting EMS based on a change in health status of the Subject 100. In some embodiments, the initiated actions may include Real-Time Transmission 140 to Critical Assistance 180. Critical Assistance 180 may include an EMS, for example.

FIG. 9A depicts an embodiment of a Health Assessment method 900 that may be implemented in one or more of the various subsystems of System 145 shown in FIG. 2, for example. In some embodiments, the Health Assessment method 900 may be implemented by the DMU. At step 905, new data is received. New data may be from one or more of the sensors or from inputs discussed above in connection with FIGS. 11, 12A, 12B, and TABLES 1 and 2, for example and without limitation. The new data may correspond to a time period. The new data 905 may be processed or analyzed locally or remotely. It should be understood that the new data may not require analysis or processing, or it may be input to algorithms with other relevant data. At block 910, the data output from block 905 is compared against one or more predetermined threshold values at block 910. In some embodiments, the method comprises detecting a health event by providing a range of potential values for the health parameter that indicates no health event has occurred and comparing the health parameter during the first time period to the range of values.

If the data from block 905 is within the threshold range, the data is added to the Subject data set at block 920. The data may be processed prior to or after block 910. If the data is not within the threshold range at block 910, it may indicate that a health event has occurred. For example, being outside the threshold range for particular values may indicate that an accident, stroke, or heart attack has occurred. At block 920, an alert is initiated. For example, a request for EMS may be output by the System 145 if an accident, stroke, or heart attack event is determined by the System 145. In some embodiments, initiating an alert comprises providing the alert to a party selected from the group consisting of the Subject, a health care provider, a contact designated by the Subject, and combinations thereof. At block 915, the data is added to the data set. In addition, the System 145 may adjust parameters, such as sampling frequency, based on the data output from block 905. For example, the sampling frequency may be modified for particular inputs, such as by reducing the sampling frequency to reduce power consumption. Similarly, at block 920 the sampling frequency may be increased to test for additional events or to verify recognized events.

Referring now to FIG. 9B, a method 940 for determining and using trends is shown. Method 940 is suitable for use in the System 145 shown in FIG. 2, for example and without limitation. At block 945, one or more trends (also referred to as a "health forecast") is determined. At block 950, the determined trend may be used to assess effects of parameters on Subject health status. For example, an increased food intake may be determined to be associated with a negative trend. Another example is a determination of a correlation between food consumption at a location and an effect on the Subject's health status. If such a correlation is determined, then this data can be used to identify health risk and advise or inform the Subject about the correlation. At block 955, a rate of change of the trend is determined. For example, the trend may be determined to be improving or worsening. At block 965, the trend information is assessed for significance, for example, by comparing with threshold values. For example, if the trend exceeds a threshold negative value it may be determined to be significant. Also, if the rate of change of a trend is determined to be worsening and exceeds a threshold value, it may be determined to be significant. In addition, if a particular parameter is correlated with a negative trend, the correlation may be significant. If the trend information is determined to be significant at block 965, a corresponding output notification is generated at block 970. For example, an output notification may be sent to the Subject 100 or a subsystem of the Ecosystems 20 or 20A such as the Ranking System 250, for example. If the trend information is not significant, the method 940 continues to block. One example that may be used to track the overall Subject health status is by using a metric that provides an indication of the overall Subject health condition, herein referred to as Health Index Parameter (HIP). The HIP is a multivariate function defined as: $HIP=f(\alpha A, \beta B, \gamma C, \ldots, t)$ where t is time and $\alpha$, $\beta$, and $\gamma$ are weighting factors for each measured health parameter (A, B, C, etc.) and may be determined in the System 145 shown in FIG. 2, for example. In some embodiments, the magnitude of the weighting factor is based on the influence of a measured parameter on health performance. The weighting factors are selected in such that when a health parameter is outside of a set of limits, it increases its HIP value. In other words, in some embodiments, high values of HIP reflect low health performance, i.e., sickness or high risk of sickness. Different types of upper and lower limits, depending on each type of health parameter, can be defined based on standard medical practices. A HIP algorithm can have different internal upper and lower thresholds with the aim to trigger early health warnings that can be used on the Ranking and Scheduling algorithms. These internal ranges can be defined in accordance with the Subject profile, historical data, and health performance, for example.

Figure 5B:
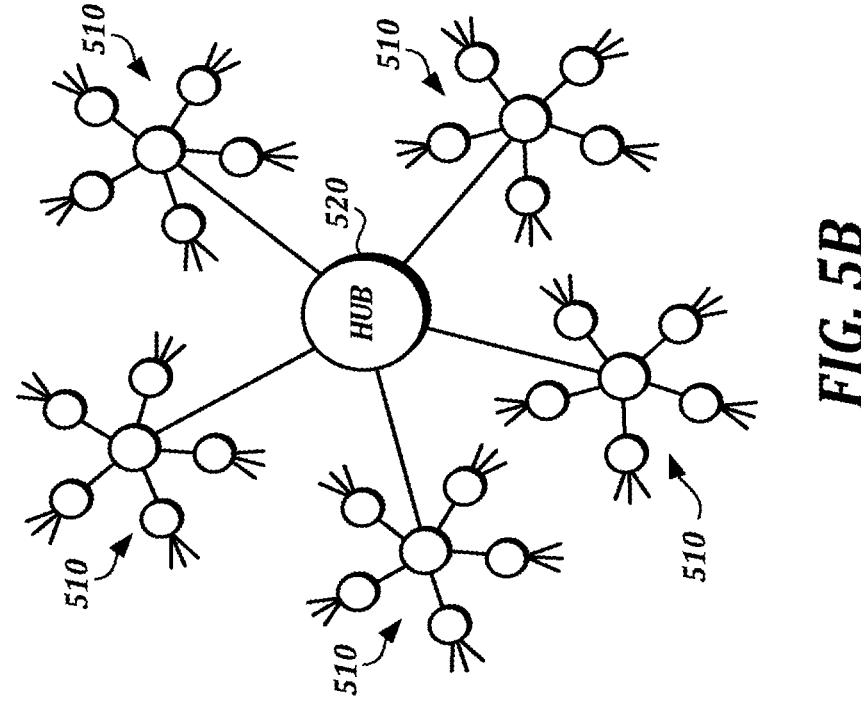
FIGS. 5A and 5B are drawings showing Ecosystem scaling in accordance with one or more aspects of the present disclosure.
Figure 5A:
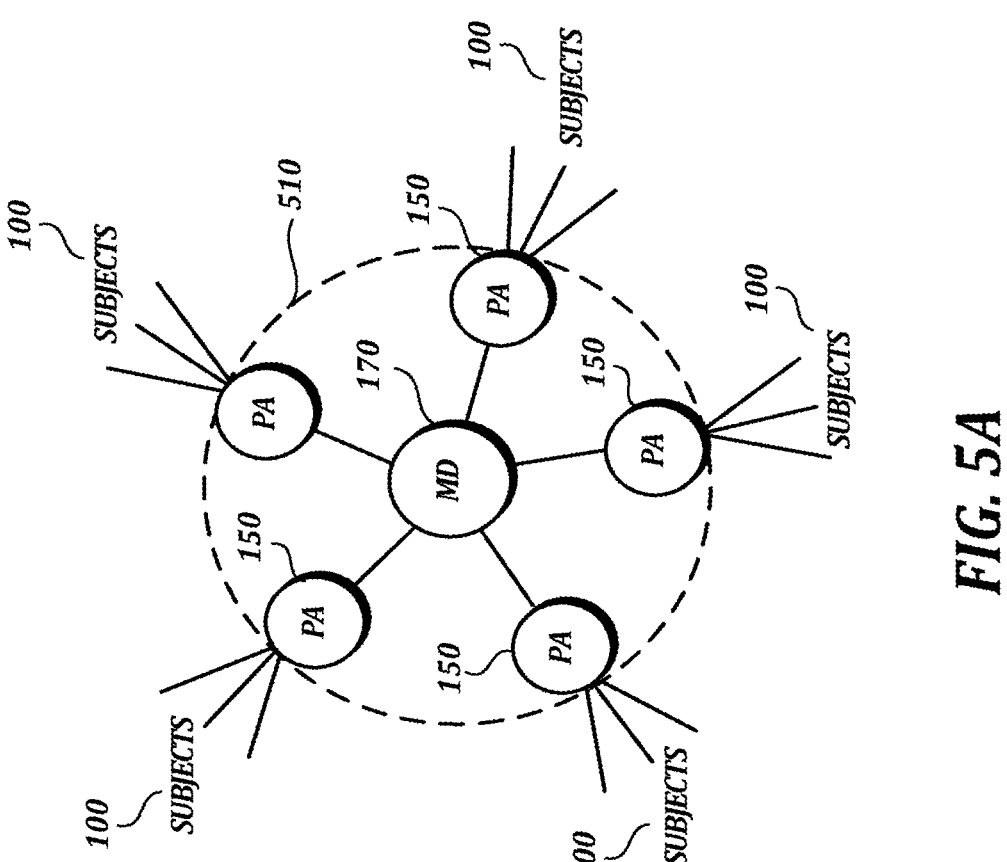

Referring now to FIG. 5A, scalability of the Ecosystem 20 is shown such that a cluster 510 includes multiple Providers 150 that are connected to an Advisor MD 170. Each Provider 150 is connected to multiple Subjects 100. In FIG. 5B, a plurality of clusters 510 are connected to a hub 520. Hub 520 may include hardware and software, such as the System 145 as well as stored data metrics that services many Subjects 100.

Figure 4:
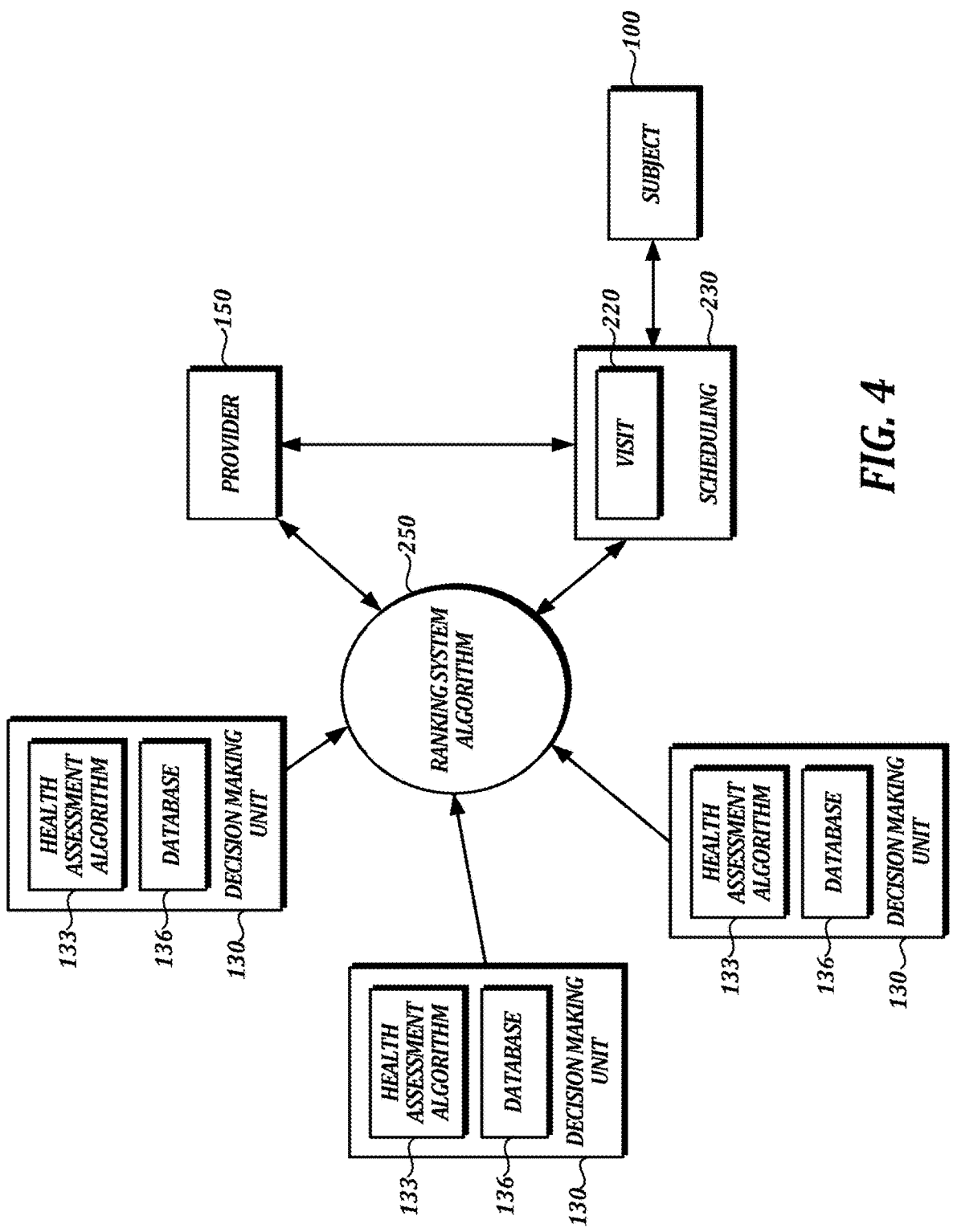
FIG. 4 is a block diagram illustrating the communication of multiple data sets in accordance with one or more aspects of the present disclosure.

Referring now to FIG. 4, a Ranking Algorithm 250 may be used to prioritize and/or schedule appointments for multiple Subjects 100 associated with, for example, a hub. The ranking algorithm may analyze the data of all Subjects 100 for a particular hub, such as a hub, for example, or another group of Subjects to assess their health conditions. Once each Subject's health status is defined, e.g., using determined HIP value and/or forecasting, cases deemed to be "critical" are collected in a ranking data set that may include Subject information and abnormal health data. Based on the HIP value as well as forecasting information and other Subject data, such as data provided by methods 900 and 940, for example, all Subjects 100 in the ranking data set are ranked from high health risk to low health risk relative to one another or in general. In some embodiments, Subjects having HIP scores corresponding to a high risk are scheduled appointments with the Provider or may be alerted to their high risk status. The Ranking Algorithm 250 may use currently known or later-developed scheduling and alerting algorithms and methods. In some embodiments, the Ranking Algorithm 250 is implemented in the System 145. In some embodiments, machine-learning algorithms are utilized with the Subject and Provider schedules and a calendar to classify and to train the Ranking Algorithm 250 to find an optimum appointment placement, booking times, overbooking percentages, and to minimize Subject waiting times. Information from the Ranking Algorithm 250 will be used, in addition to conventional appointment systems, to schedule an appointment or visit for the Subject with the Provider. Based on the priority assigned by the ranking algorithm (e.g., index and time frame) as well as available provider time slots, a communication (e.g., voice, video, text) is issued to the Subject to negotiate the appointment date.

In one embodiment of Ranking Algorithm 250 or method, includes generating a first health parameter for a first Subject and a second health parameter for a second Subject and comparing the first health parameter to the second health parameter. The first health parameter and the second health parameter may be generated by providing and/or receiving a first input and a second input, each input obtained during a first time period and each input being independently selected from the group consisting of: a food data input, a mood data input, a vital sign data input, a biometric data input, a gait analysis data input, a genotype data input, a lifestyle data input, an environment data input, a biological data input; and generating a health parameter using both the first input and the second input. The health parameter is indicative of the Subject's health during the first time period. The food data input may be obtained by analyzing at least one portion of food consumed by the Subject during the first time period. The mood data input may be obtained through active input by the Subject during a first time period. It will be understood that other inputs and methods may be used to generate health parameters. More than one health parameter may be generated for a Subject. More than one health parameter may be compared. Health parameters may be determined and/or compared for a plurality of Subjects.

As shown in FIG. 4, if the Subject 100 has a health issue or situation that has not been identified, the Subject 100 communicates with the health Provider 150 to schedule an appointment for a conventional visit. During this visit, the Provider 150 may have tests performed on the Subject 100, record the care provided to the Subject 100, and gather additional data and aggregate it to the Subject's historical database such that it is accessible to or included within the System 145.

Figure 10:
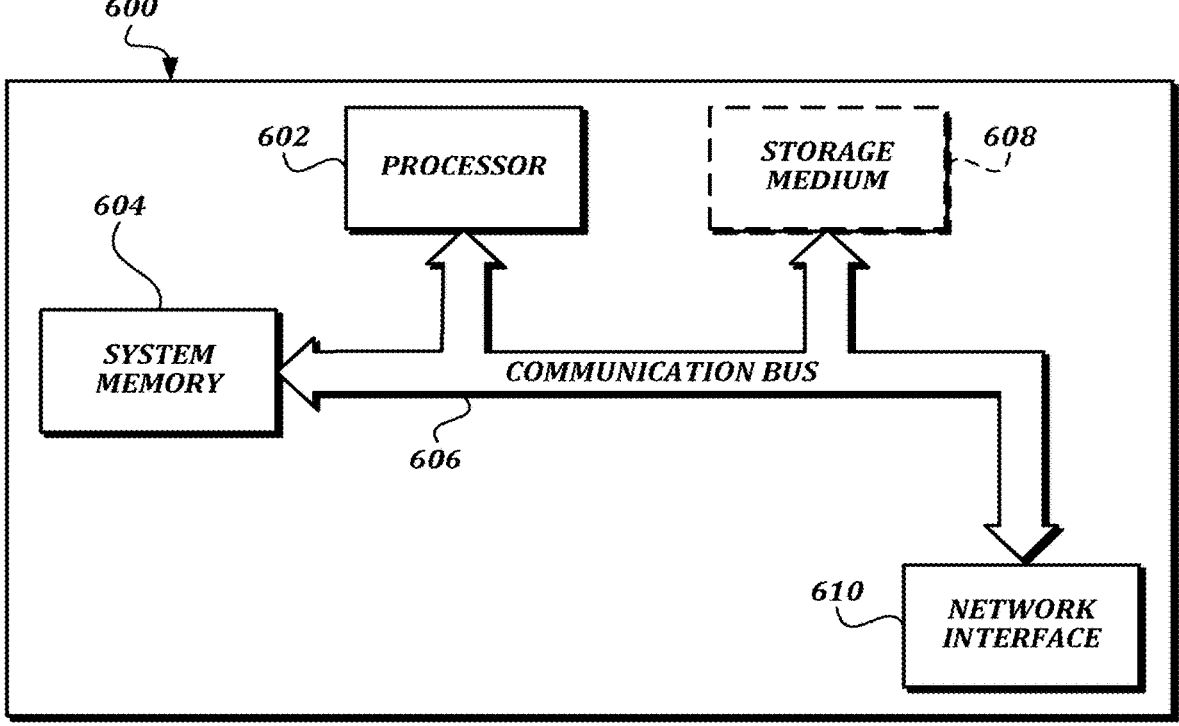
FIG. 10 is a block diagram illustrating aspects of an exemplary computing device appropriate for use with one or more aspects of the present disclosure.

FIG. 10 is a block diagram that illustrates aspects of an exemplary computing device 600, appropriate for use with embodiments of the present disclosure such as the Technology 110, the Data Analytics, and the DMU. While FIG. 10 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 600 may be any one of any number of currently available or yet to be developed devices.

In its most basic configuration, the computing device 600 includes at least one processor 602 and a system memory 604 connected by a communication bus 606. Depending on the exact configuration and type of device, the system memory 604 may be volatile or nonvolatile memory, such as read-only memory ("ROM"), random access memory ("RAM"), EEPROM, flash memory, or similar memory technology. Those of ordinary skill in the art and others will recognize that system memory 604 typically stores data and/or program modules that are immediately accessible to and/or currently being operated on by the processor 602. In this regard, the processor 602 may serve as a computational center of the computing device 600 by supporting the execution of instructions.

As further illustrated in FIG. 10, the computing device 600 may include a network interface 610 comprising one or more components for communicating with other devices over a network. Embodiments of the present disclosure may access basic services that utilize the network interface 610 to perform communications using common network protocols. The network interface 610 may also include a wireless network interface configured to communicate via one or more wireless communication protocols, such as WiFi, 2G, 3G, LTE, WiMAX, Bluetooth, and/or the like.

In the exemplary embodiment depicted in FIG. 10, the computing device 600 also includes a storage medium 608. However, services may be accessed using a computing device that does not include means for storing data on a local storage medium. Therefore, the storage medium 608 depicted in FIG. 10 is represented with a dashed line to indicate that the storage medium 608 is optional. In any event, the storage medium 608 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and nonvolatile and removable and nonremovable media implemented in any method or technology capable of storing information, such as computer-readable instructions, data structures, program modules, or other data.

In this regard, the system memory 604 and storage medium 608 depicted in FIG. 10 are merely examples of computer-readable media.

Suitable implementations of computing devices that include a processor 602, system memory 604, communication bus 606, storage medium 608, and network interface 610 are known and commercially available. For ease of illustration and because it is not important for an understanding of the claimed subject matter, FIG. 10 does not show some of the typical components of many computing devices. In this regard, the computing device 600 may include input devices, such as a keyboard, keypad, mouse, microphone, touch input device, touch screen, tablet, and/or the like. Such input devices may be coupled to the computing device 600 by wired or wireless connections including RF, infrared, serial, parallel, Bluetooth, USB, or other suitable connection protocols using wireless or physical connections. Similarly, the computing device 600 may also include output devices such as a display, speakers, printer, etc. Since these devices are well known in the art, they are not illustrated or described further herein.

As will be appreciated by one skilled in the art, the specific routines described above in the flowcharts may represent one or more of any number of processing strategies such as event-driven, interrupt-driven, multi-tasking, multi-threading, and the like. As such, various acts or functions illustrated may be performed in the sequence illustrated, in parallel, or, in some cases, omitted. Likewise, unless explicitly stated, the order of processing is not necessarily required to achieve the features and advantages, but is provided for ease of illustration and description. Although not explicitly illustrated, one or more of the illustrated acts or functions may be repeatedly performed depending on the particular strategy being used. Further, these figures may graphically represent code to be programmed into a computer-readable storage medium associated with a computing device. Various principles, representative embodiments, and modes of operation of the present disclosure have been described in the foregoing description. However, aspects of the present disclosure that are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the claimed subject matter.

After discussing the details of various aspects of the present disclosure, it should be understood that aspects of the following description may be presented in terms of logic and operations that may be performed by electronic components. These electronic components, which may be grouped in a single location or distributed over a wide area, generally include controllers, microcontrollers, control units, processors, microprocessors, etc. It will be appreciated by one skilled in the art that any logic described herein may be implemented in a variety of configurations, including but not limited to hardware, software, and combinations thereof. The hardware may include but is not limited to, analog circuitry, digital circuitry, processing units, application-specific integrated circuits (ASICs), and the like, and combinations thereof. In circumstances in which the components of the system are distributed, the components are accessible to each other via communication links.

In general, functionality of devices described herein may be implemented in computing logic embodied in hardware or software instructions, which can be written in a programming language, such as C, C++, COBOL, JAVA™, PHP, Perl, HTML, CSS, JavaScript, VBScript, ASPX, Microsoft .NET™ languages such as C#, and/or the like. Computing logic may be compiled into executable programs or written in interpreted programming languages. Generally, functionality described herein can be implemented as logic modules that can be duplicated to provide greater processing capability, merged with other modules, or divided into submodules. The computing logic can be stored in any type of computer-readable medium (e.g., a non-transitory medium such as a storage medium) or computer storage device and be stored on, read, and executed by one or more general-purpose or special-purpose processors.

In one aspect of the present disclosure, a method of evaluating the health of a Subject 100 is provided. The method includes providing and/or receiving a first input that is at least one of a mood data input and a food data input, providing and/or receiving a second input obtained during the first time period and generating a health parameter using both the first input and the second input, wherein the health parameter is indicative of the Subject's health during the first time period. The health parameter may be, for example, the HIP algorithm. The mood data input is obtained through an active input by the Subject 100 during the first time period. For example, the mood data input may be obtained using the mood inputs described in FIGS. 12A and 12B. The mood data input may be, for example, manually selected or entered by the Subject 100 based on the Subject's perceived mood. The food data input is obtained by analyzing at least one portion of food consumed by the Subject 100 during the first time period. The duration of the first time period may depend on a sampling frequency used by the System 145. The second input is selected from the group consisting of: a vital sign data input, a physical sensor data input, a biometric data input, a genotype data input, a lifestyle data input, an environment data input, a gait analysis data input, and a biological data input, such as, and without limitation, the inputs listed in TABLE 2.

In one embodiment, the mood data input includes information regarding a psychological condition of the Subject 100. For example, the psychological condition of the Subject 100 may be psychological disorder of the Subject 100. The psychological condition may be a mood. In one embodiment, the psychological condition includes an indication of a mood state selected from the group consisting of anxiety, stress, anger, frustration, happiness, sadness, depression, and combinations thereof.

In one embodiment, the active input comprises the Subject providing an intensity and a frequency of data input that indicates the mood state, such as, but not limited to, the embodiments depicted in FIGS. 12A and 12B. In one embodiment, the user's mood is conveyed to a computing device, by a method comprising: providing a sensor configured to receive physical input from the user (e.g., by shaking or tapping the sensor); sensing a physical motion of the user using the sensor configured to receive physical input; and correlating the sensed physical motion with a particular mental state (e.g., happy, sad, stressed), such as, but not limited to, the embodiments depicted in FIGS. 12A and 12B.

In one embodiment, the mood data input includes information regarding a fatigue level or a concentration level of the Subject. In one embodiment, the active input comprises testing the Subject using a game or a task. In one embodiment, the game or the task is implemented in an electronic device. In one embodiment, the food data input includes information selected from the group consisting of a nutrition index, an intake frequency, a weight, a volume and combinations thereof. In one embodiment, the nutrition index is generated by analyzing a digital image of the portion of food. In one embodiment, the identity of a portion of food is determined by a method comprising: obtaining a digital image of the portion of food; determining the type of food by comparing the digital image to a database of known food types, wherein the determination may rely on color, shape, texture, or other detectable characteristics of the food portion that can be conveyed by the digital image; prompting a user to verify the determined identity of the food; prompting the user to modify the determined identity of the food along with additional characteristics of the food (e.g., amount, specific food type, etc.); and determining the composition of the portion of food, including type of food and nutritional content (e.g., calories, fat, protein, etc.).

In some embodiments, the method further comprises repeating the steps of the method a plurality of times during subsequent time periods in order to generate a plurality of health parameters, each health parameter being indicative of the Subject's health during a specific time period, wherein the plurality of health parameters define a health parameter history of the patient over the time periods. The time periods may have different durations. In some embodiments, the durations are determined by the System 145.

In some embodiments, the vital sign data input includes information related to a characteristic of the Subject selected from the group consisting of heart rate, pulse, blood pressure, blood pressure index, body temperature, breathing, activity, sleep, barometric pressure for altimetry, and combinations thereof. In some embodiments, the physical sensor data input includes information related to a characteristic of the Subject selected from the group consisting of foot pressure, acceleration of any body part or center of mass, lateral motion, gait analysis, and combinations thereof. In some embodiments, the biometric data input includes information related to a characteristic of the Subject selected from the group consisting of age, gender, height, race, metabolic profile, metabolic panel, and combinations thereof.

In some embodiments, the genotype data input includes information related to a characteristic of the subject selected from the group consisting of genetic composition, genomic profile, biomarkers, and combinations thereof. In some embodiments, the lifestyle data input includes information related to a characteristic of the Subject selected from the group consisting of work, drinking/smoking/sating habits, other habits, activities, hobbies, sports, education, and combinations thereof.

In some embodiments, the environmental data input includes information related to a characteristic of the Subject selected from the group consisting of geographic information indicative of a geographic position of the Subject, weather conditions near the Subject, pollution near the Subject, type of location including home, work, travel, restaurant, bar, gym, park, economic environmental conditions, social environmental conditions, political environmental conditions, and combinations thereof.

In some embodiments, the biological data input includes information related to a characteristic of the Subject selected from the group consisting of a skin moisture level, a blood oxygen level, a blood carbon dioxide level, a blood glucose level, a body weight, a body fatty tissue level, an electrocardiogram, an electromyogram, a urine content, a fecal content, an image of the Subject, and combinations thereof.

In some embodiments, the first input and the second input include temporal data indicating the time at which the first input and the second input were obtained. The method may further include reporting the health parameter to a party selected from the group consisting of the Subject, a health care provider, a contact designated by the Subject, a health care information system, an insurance provider, an emergency medical system, a medical facility, and combinations thereof.

In another aspect, a method of evaluating the health of a Subject is provided. In one embodiment, the method includes providing a first input that is a geographic information data input, providing a second input obtained during a first time period, and generating a health parameter using both the first input and the second input. The geographic information input is indicative of a geographic position of the Subject during a first time period. The second input is selected from the group consisting of: a food data input, a mood data input, wherein the mood data input is obtained through active input by the Subject during a first time period, a vital sign data input, a gait analysis data input, a biometric data input, a genotype data input, a lifestyle data input, an environment data input, and a biological data input. The health parameter is indicative of the Subject's health during the first time period. The food data input may be obtained by analyzing at least one portion of food consumed by the Subject during the first time period. For example and without limitation, the food data input may be obtained using the food tool disclosed in FIG. 12.

In another aspect, a method of evaluating the health of a Subject is provided. In one embodiment, the method includes: providing a first input that is a mood data input, wherein the mood data input is obtained through active input by the Subject during a first time period; providing a second input obtained during the first time period, and generating a health parameter using both the first input and the second input. The second input is selected from the group consisting of: a food data input, a vital sign data input, a gait analysis data input, a biometric data input, a genotype data input, a lifestyle data input, an environment data input, and a biological data input. The food data input is obtained by analyzing at least one portion of food consumed by the Subject during a first time period. The health parameter is indicative of the Subject's health during the first time period.

In yet another aspect, a method of evaluating the health of a plurality of Subjects is provided. In one embodiment, the method includes: generating a first health parameter for a first Subject and a second health parameter for a second Subject. The following steps may be used to generate both the first health parameter and the second health parameter: providing a first input and a second input, each input obtained during a first time period and each input being independently selected from the group consisting of: a food data input, wherein the food data input is obtained by analyzing at least one portion of food consumed by the Subject during the first time period, a mood data input, wherein the mood data input is obtained through active input by the Subject during a first time period, a vital sign data input, a gait analysis data input, a biometric data input, a genotype data input, a lifestyle data input, an environment data input, and a biological data input; and generating a health parameter using both the first input and the second input, wherein the health parameter is indicative of the Subject's health during the first time period; and comparing the first health parameter to the second health parameter.

In one embodiment, the method further comprises ranking the first health parameter and the second health parameter with regard to the urgency with which the first Subject and the second Subject require medical attention. Urgency may be based on trends or other information as determined by the methods disclosed in FIGS. 9A and 9B, for example, and without limitation.

In one embodiment, the method further comprises generating a third health parameter for a third Subject using steps (i) and (ii), and comparing the third health parameter to the first health parameter and the second health parameter.

Exemplary Scenarios

The provided examples are used to illustrate the embodiments of the present disclosure and should not be construed as limiting.

Example #1: A Subject 100 has inputs that indicate the Subject has a sad mood, decreased food consumption; and sensor inputs indicate the Subject has congestion and a fever over a time period. A worsening trend is determined that is determined to be significant by the method 940. An appointment is scheduled by the Scheduling Algorithm. The Subject 100 is assessed by the Provider 150 for cold and flu symptoms. Based on physiological markers and environment markers such as data of flu outbreaks in local regions, an assessment is made based on probability of various diagnoses and treatment is rendered.

Example #2: A Subject 100 presents in person to the Provider 150 with a headache and fatigue. The subsystems of the Ecosystem 20 check a log for previous impact or trauma to the Subject 150 based on accelerometer sensor data and oral examination. It is determined that the Subject 100 has a history of mild impact in the last 24 hours. The Subject is recommended to a specialist, and an appointment is scheduled for further observation.

Example #3: The Subject 100 is assessed for a yearly physical. The physical examination is completed by a Provider 150, and comments are input into the system to be analyzed alongside vital sign data input, biometric data input, genotype data input, lifestyle data input, gait analysis, environmental data input, biological data input, and metabolic data input collected about the person. The assessment is logged and compiled in the system with key health improvements and declines highlighted and observed. Recommendations are made to the Subject 100, and a plan is logged.

Example #4: A Subject 100 presents with rapid weight loss. The System 145 automatically communicates this rapid deviation from a median metric to the Provider 150; a follow-up visit is scheduled. This follow up occurs over e-mail and it is determined that the Subject is feeling stressed about increased workloads. Data compiled from Human Intake software such as Food and Mood shown in FIGS. 11 and 12 reveals a drastic change in diet and psychological wellbeing of the Subject 100. A Life Coach, such as a nutritionist and/or a psychologist, is added to the Ecosystem 20 to help deliver coping methods and lifestyle changes.

Example #5: An elder Subject 100 requests consultation on some long-term life planning decisions. The Subject 100 has used the system for 20 years. Based on the extensive data collected and analyzed by the Ecosystem 20, there are some predictive trends and probabilities of potential health risk factors and how best to manage geriatric medical care for this Subject 100. The consultation along with the recommendations for the collected data are used by the Subject and their family to make recommendations of where the Subject should live, what type of insurance to have, and what type of activities to enroll and participate in for the highest quality of life.

In view of the disclosure, it will be appreciated that the Ecosystem 20 may be interactive and social and may provide guidance, support, routine care, emergency services and promote general healthy living through incremental feedback loops and positive reinforcement methods. It will also be appreciated that the Ecosystem 20 may allow for a shift of perspective from the current methods of health care delivery. It provides novel approaches to treating people, not simply symptoms and disease. It may provide long-term support and engagement with Subjects 100 and may enable a Subject 100 to live a healthier lifestyle through a more detailed and complete analysis of the Subject's health and continuous monitoring of deviations from a defined health baseline of the Subject 100. The Ecosystem 20 may also allow for early detection and intervention with respect to disease, injury, and declined health to prevent long-term damage to the health of a Subject 100 using state of the art technology, data analysis, encouraged engagement in the services and programs of the system, and world class care provided by licensed medical professionals trained to practice medicine combined with technology platforms. The Ecosystem 20 may provide for data of a Subject 100 to be analyzed in a way that helps Providers 150 identify problems early and helps guide a Subject 100 to better health and provides more comprehensive care. Over time, care can be optimized, improved, and more Subjects 100 can be covered with the same or fewer resources.

Though exemplary calculations and applications are discussed above, one of ordinary skill in the art will understand that these examples are to illustrate the capabilities of the system and should not be seen as limiting.

The principles, representative embodiments, and modes of operation of the present disclosure have been described in the foregoing description. However, aspects of the present disclosure that are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A system for improving health of a subject, the system comprising:

a wearable computing device; and a decision making unit (DMU) computing system communicatively coupled to the wearable computing device via a network;

wherein the wearable computing device is associated with the subject;

wherein the wearable computing device comprises a plurality of sensors, and wherein the plurality of sensors includes one or more sensors that generate values that are relevant to a recognized event and one or more sensors that generate values that are not relevant to the recognized event;

wherein the wearable computing device is configured to:

collect values generated by the plurality of sensors of the wearable computing device; and transmit the values generated by the plurality of sensors to the DMU computing system; and wherein the DMU computing system is configured to:

receive the values generated by the plurality of sensors of the wearable computing device;

predicting a presence or absence of the recognized event based on the values generated by the plurality of sensors;

in response to predicting the presence of the recognized event, cause the wearable computing device to increase sampling frequencies of the one or more sensors of the wearable computing device that generate values that are relevant to the recognized event while leaving unchanged sampling frequencies of the one or more sensors of the wearable computing device that generate values that are not relevant to the recognized event to verify the recognized event while keeping increased power consumption to a minimum.

2. The system of claim 1, further comprising an AI system, and wherein causing the wearable computing device to increase sampling frequencies of the one or more sensors of the wearable computing device that generate values that are relevant to the recognized event includes:

determining, using the AI system, a level of detail desired from the one or more sensors; and causing the wearable computing device to increase the sampling frequencies of the one or more sensors of the wearable computing device that generate values that are relevant to the recognized event to frequencies corresponding to the level of detail desired.

3. The system of claim 1, wherein the DMU computing system is further configured to:

in response to predicting the absence of the recognized event, cause the wearable computing device to reduce sampling frequencies of the one or more sensors of the wearable computing device that generate values that are relevant to the recognized event to reduce power consumption.

4. The system of claim 3, further comprising an AI system, and wherein causing the wearable computing device to reduce sampling frequencies of the one or more sensors of the wearable computing device that generate values that are relevant to the recognized event to reduce power consumption includes:

determining, using the AI system, a level of detail desired from the one or more sensors; and causing the wearable computing device to decrease the sampling frequencies of the one or more sensors of the wearable computing device that generate values that are relevant to the recognized event to frequencies corresponding to the level of detail desired.

5. The system of claim 1, further comprising a smartphone communicatively coupled to the DMU computing system;

wherein the smartphone includes a plurality of smartphone sensors;

wherein the smartphone is associated with the subject; and wherein the smartphone is configured to:

collect values from the plurality of smartphone sensors; and transmit the values collected from the plurality of smartphone sensors to the DMU computing system.

6. The system of claim 5, wherein the plurality of smartphone sensors include one or more of:

a positioning sensor; and a motion sensor.

7. The system of claim 5, wherein the wearable computing device is communicatively coupled to the DMU computing system via the smartphone.

8. The system of claim 1, wherein the plurality of sensors includes one or more of:

a skin moisture sensor;

a temperature sensor;

a blood pressure sensor;

an accelerometer;

a heart rate sensor;

a microphone;

a barometer;

an oximetry sensor;

an electrocardiogram (ECG) sensor;

a body fat sensor;

a glucose sensor; and a weight sensor.

9. The system of claim 1, wherein the wearable computing device further includes at least one subject status sensor, and wherein transmitting the values generated by the plurality of sensors to the DMU computing system includes:

refraining from transmitting values generated by the plurality of sensors during time periods in which the subject status sensor indicates that the values are not indicative of subject health.

10. The system of claim 9, wherein the at least one subject status sensor includes at least one of a motion sensor, a heart rate sensor, and a temperature sensor.

11. The system of claim 1, wherein the plurality of sensors for at least one wearable device includes a foot pressure sensor.

12. The system of claim 1, wherein the plurality of sensors for at least one wearable device includes:

a temperature sensor;

an accelerometer;

a heart rate sensor;

a microphone;

a barometer;

an oximetry sensor; and an electrocardiogram (ECG) sensor.

13. The system of claim 12, wherein the recognized event is a heart attack, and wherein the one or more sensors that generate values that are relevant to the recognized event include at least one of the heart rate sensor, the ECG sensor, the oximetry sensor, and the barometer.

14. The system of claim 12, wherein the recognized event is a fall, and wherein the one or more sensors that generate values that are relevant to the recognized event include at least one of the accelerometer, the heart rate sensor, the microphone, and the barometer.

15. A method for improving health of a plurality of subjects, the method comprising:

receiving, by a decision making unit (DMU) computing device, values from a wearable computing device, wherein the wearable computing device includes a plurality of sensors that generate the values, and wherein the plurality of sensors includes one or more sensors that generate values that are relevant to a recognized event and one or more sensors that generate values that are not relevant to the recognized event;

predicting, by the DMU computing device, a presence or absence of the recognized event based on the values received from the wearable computing device;

in response to predicting the presence of the recognized event, causing, by the DMU computing device, the wearable computing device to increase sampling frequencies of the one or more sensors of the wearable computing device that generate values that are relevant to the recognized event while leaving unchanged sampling frequencies of the one or more sensors of the wearable computing device that generate values that are not relevant to the recognized event to verify the recognized event while keeping increased power consumption to a minimum.

16. The method of claim 15, wherein causing the wearable computing device to increase sampling frequencies of the one or more sensors of the wearable computing device that generate values that are relevant to the recognized event includes:

determining, using an AI system, a level of detail desired from the one or more sensors; and causing the wearable computing device to increase the sampling frequencies of the one or more sensors of the wearable computing device that generate values that are relevant to the recognized event to frequencies corresponding to the level of detail desired.

17. The method of claim 15, further comprising:

in response to predicting the absence of the recognized event, causing, by the DMU computing device, the wearable computing device to reduce sampling frequencies of the one or more sensors of the wearable computing device that generate values that are relevant to the recognized event to reduce power consumption.

18. The method of claim 17, wherein causing the wearable computing device to reduce sampling frequencies of the one or more sensors of the wearable computing device that generate values that are relevant to the recognized event to reduce power consumption includes:

determining, using an AI system, a level of detail desired from the one or more sensors; and causing the wearable computing device to decrease the sampling frequencies of the one or more sensors of the wearable computing device that generate values that are relevant to the recognized event to frequencies corresponding to the level of detail desired.

\* \* \* \* \*